US009427022B2

(12) United States Patent  (10) Patent No.: US 9,427,022 B2
Levin et al.  (45) Date of Patent: Aug. 30, 2016

(54) ELECTRONIC VAPORIZING DEVICE AND METHODS FOR USE

(71) Applicant: UpToke, LLC, Berkeley, CA (US)

(72) Inventors: Jason R. Levin, Berkeley, CA (US); Adam J. Tavin, East Palo Alto, CA (US); Artem Mishin, Pacifica, CA (US); Howard Allen Wilson, Campbell, CA (US); Saroj Kumar Sahu, Mountain House, CA (US); James Juma, Palo Alto, CA (US)

(73) Assignee: UPTOKE, LLC, Berkeley, CA (US)

( * ) Notice: Subject to any disclaimer, the term of this patent is extended or adjusted under 35 U.S.C. 154(b) by 542 days.

(21) Appl. No.: 13/797,905

(22) Filed: Mar. 12, 2013

(65) Prior Publication Data

US 2013/0298905 A1  Nov. 14, 2013

Related U.S. Application Data

(60) Provisional application No. 61/609,813, filed on Mar. 12, 2012.

(51) Int. Cl.
 *A24F 47/00* (2006.01)
 *A61M 15/06* (2006.01)

(52) U.S. Cl.
 CPC ............ *A24F 47/008* (2013.01); *A24F 47/002* (2013.01); *A61M 15/06* (2013.01)

(58) Field of Classification Search
 CPC .............. A24F 9/04; A24F 9/06; A24F 9/08; A24F 47/00; A24F 13/02; A24F 13/06; A24F 47/008; A24F 47/002; A61M 15/06; B02C 18/08
 USPC ............ 128/202.21, 203.26; 241/169, 169.1, 241/168, 69, 70
 See application file for complete search history.

(56) References Cited

U.S. PATENT DOCUMENTS 3,352,309 A * 11/1967 Kaul .............................. 131/224
3,853,132 A * 12/1974 Patton ........................... 131/243
(Continued)

FOREIGN PATENT DOCUMENTS

RU  94815 U1  6/2010
RU  111765 U1  12/2011

OTHER PUBLICATIONS

International Search Report and Written Opinion of corresponding International Application No. PCT/US2013/030610, dated Aug. 29, 2013. 3 pages.
(Continued)

*Primary Examiner* — Jason Flick
*Assistant Examiner* — Margaret Luarca
(74) *Attorney, Agent, or Firm* — Kilpatrick Townsend & Stockton LLP

(57) ABSTRACT

Devices and methods for vaporizing active ingredients of a selected substance for inhalation using a portable vaporization device are provided herein. In certain aspects, the device includes a portable power source, a heating portion, an inhalation sensor, a temperature sensor, a distal light source, and a grinding portion. In response to an inhalation by a user, the power source energizes a heating element of the heating portion so as to heat air flow to a desired vaporization temperature within a few seconds of detecting inhalation, using convection and radiative heating. The device may include a receptacle for receiving a cartridge containing a pre-prepared substance, such as a liquid, gel, powder, or solid brick, and a grinding portion to allow a user to grind intact portions of cellulose-based material into smaller pieces to facilitate vaporization by manually rotating portions of the device relative to each other.

27 Claims, 23 Drawing Sheets

(56) References Cited

U.S. PATENT DOCUMENTS

| | | | |
|---|---|---|---|
| 4,697,749 A * | 10/1987 | Holcomb | A47J 42/34 241/169 |
| 4,947,874 A * | 8/1990 | Brooks et al. | 131/329 |
| 5,535,735 A | 7/1996 | McPherson | |
| D405,219 S | 2/1999 | Dal Monte | |
| 5,878,752 A * | 3/1999 | Adams et al. | 131/329 |
| 6,095,153 A | 8/2000 | Kessler et al. | |
| D479,018 S | 8/2003 | Sgariboldi | |
| D533,309 S | 12/2006 | Nobuto et al. | |
| D585,489 S | 1/2009 | Han | |
| D598,496 S | 8/2009 | Ikeda | |
| D617,050 S | 6/2010 | Lou | |
| 7,832,410 B2 | 11/2010 | Hon | |
| D628,636 S | 12/2010 | Wang | |
| 7,997,280 B2 | 8/2011 | Rosenthal | |
| D656,545 S | 3/2012 | Hung | |
| 8,393,563 B2 * | 3/2013 | Chaoui | B02C 18/08 241/168 |
| D681,038 S | 4/2013 | Tomohiro | |
| D684,311 S | 6/2013 | Liu | |
| 2008/0023003 A1 | 1/2008 | Rosenthal | |
| 2009/0293892 A1 * | 12/2009 | Williams | A24F 47/008 131/328 |
| 2010/0242974 A1 | 9/2010 | Pan | |
| 2011/0036346 A1 | 2/2011 | Cohen et al. | |
| 2011/0097060 A1 | 4/2011 | Buzzetti | |
| 2011/0168194 A1 | 7/2011 | Hon | |
| 2011/0192399 A1 | 8/2011 | Wilke et al. | |
| 2011/0236002 A1 | 9/2011 | Oglesby et al. | |
| 2011/0265806 A1 | 11/2011 | Alarcon et al. | |
| 2012/0048266 A1 * | 3/2012 | Alelov | 128/202.21 |
| 2012/0097774 A1 * | 4/2012 | Hainbach | 241/101.2 |
| 2012/0125350 A1 * | 5/2012 | Braveman | 131/202 |
| 2012/0325227 A1 * | 12/2012 | Robinson et al. | 131/328 |
| 2014/0261494 A1 | 9/2014 | Scatterday | |

OTHER PUBLICATIONS

International Preliminary Report on Patentability mailed Sep. 25, 2014, from PCT application No. PCT/US2013/030610 (6 pages).
Notice of Allowance mailed Nov. 12, 2014, from U.S. Appl. No. 29/446,706 (9 pages).

* cited by examiner

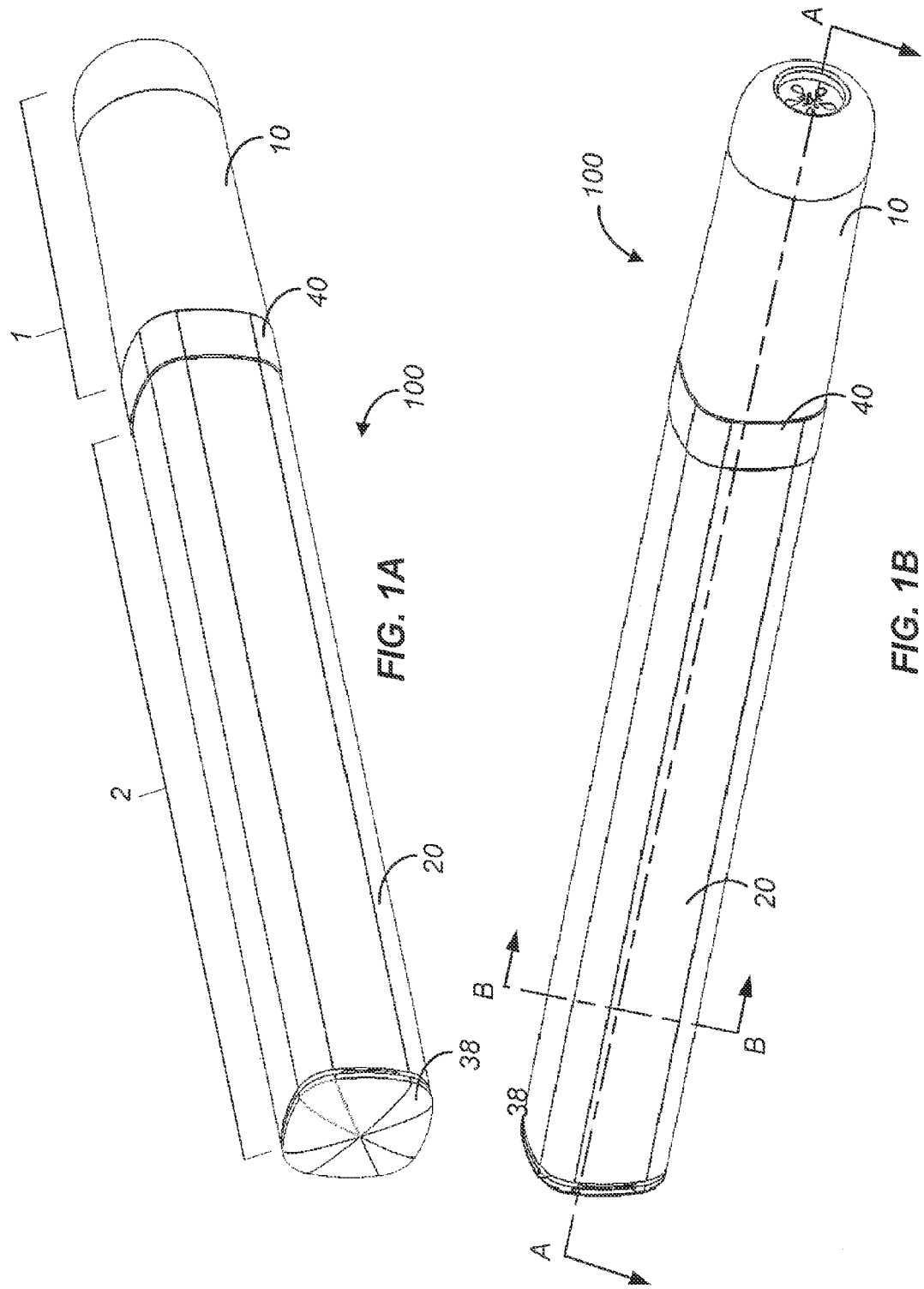

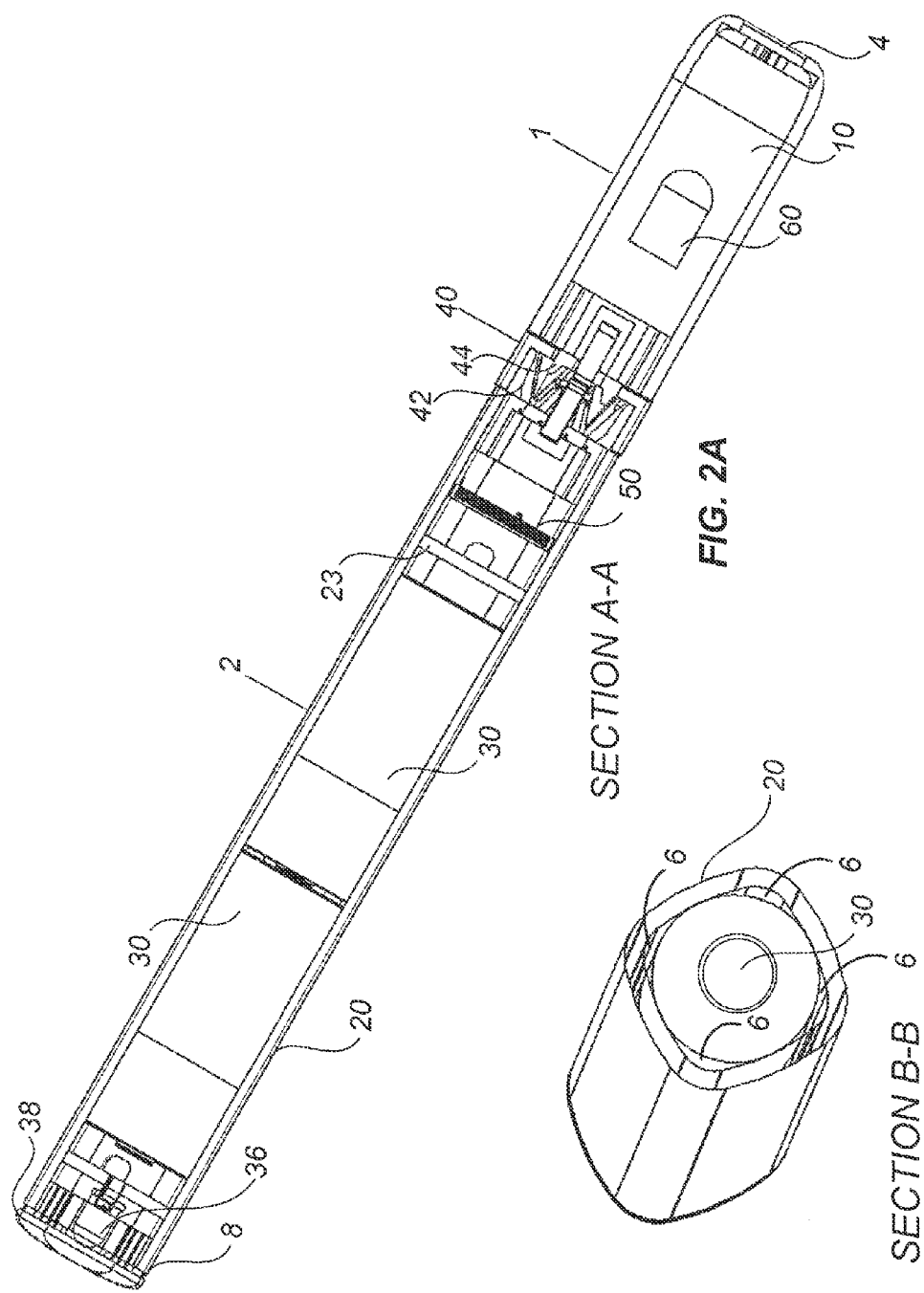

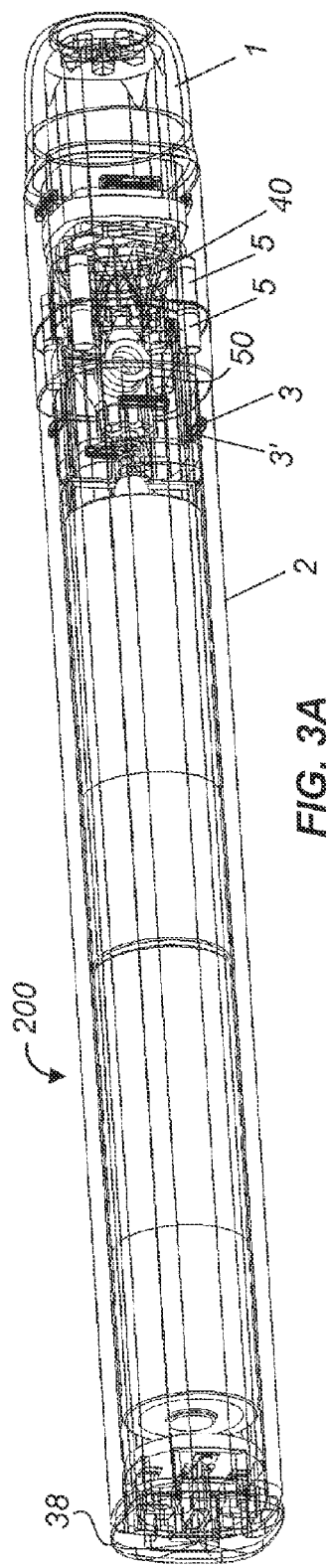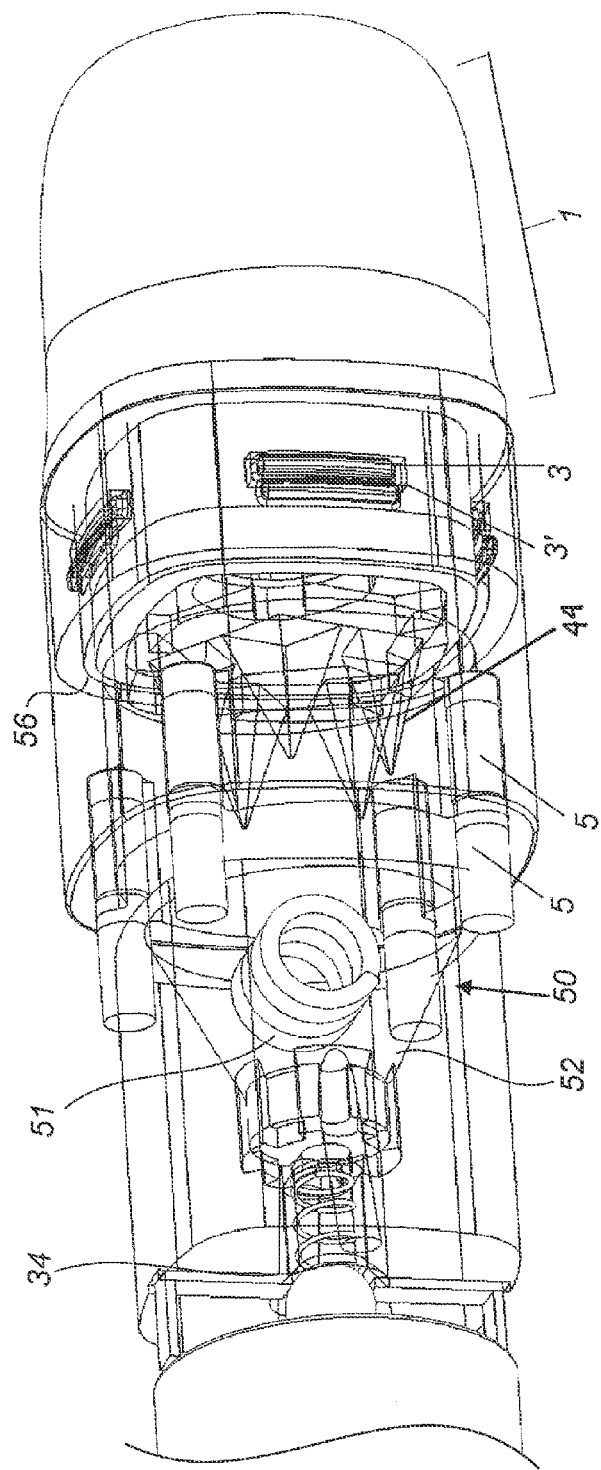
FIG. 3A
FIG. 3B

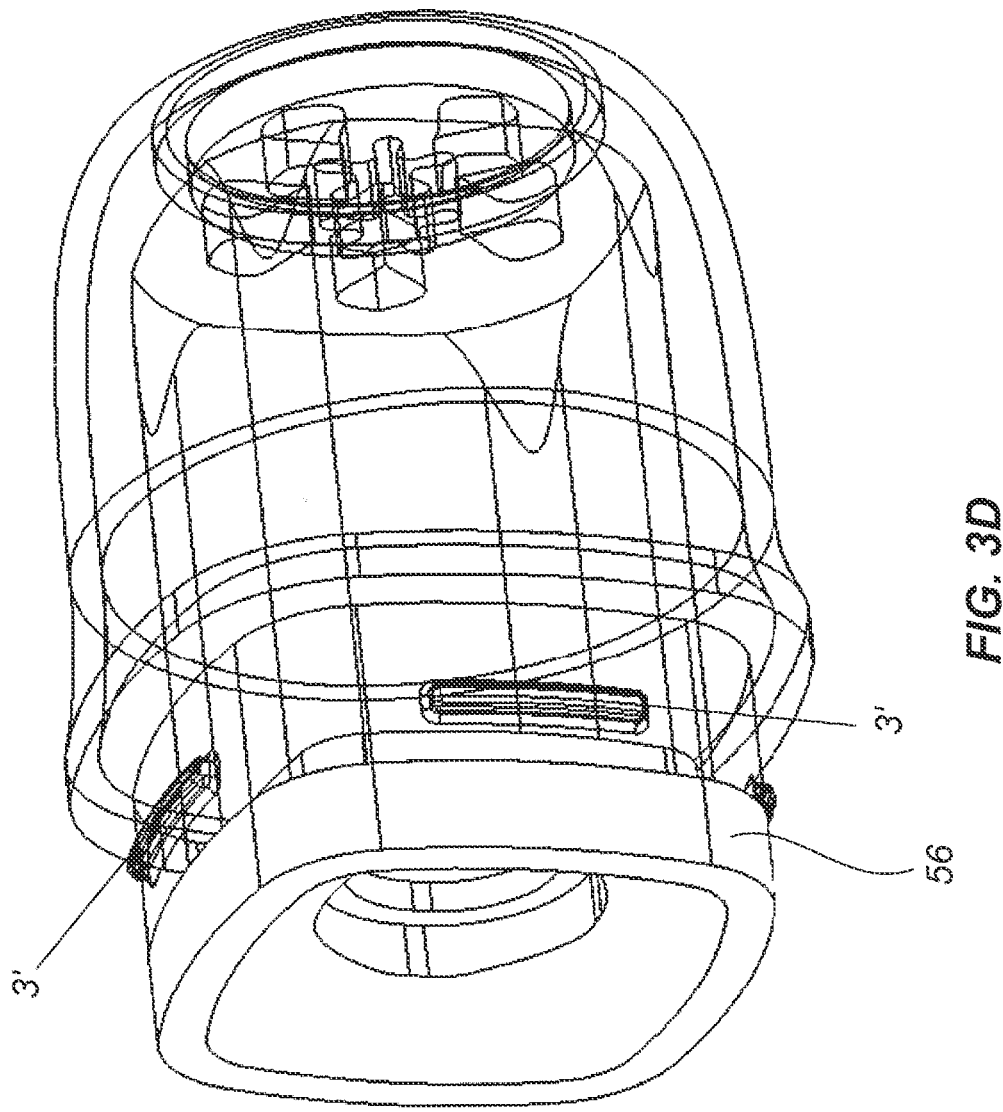

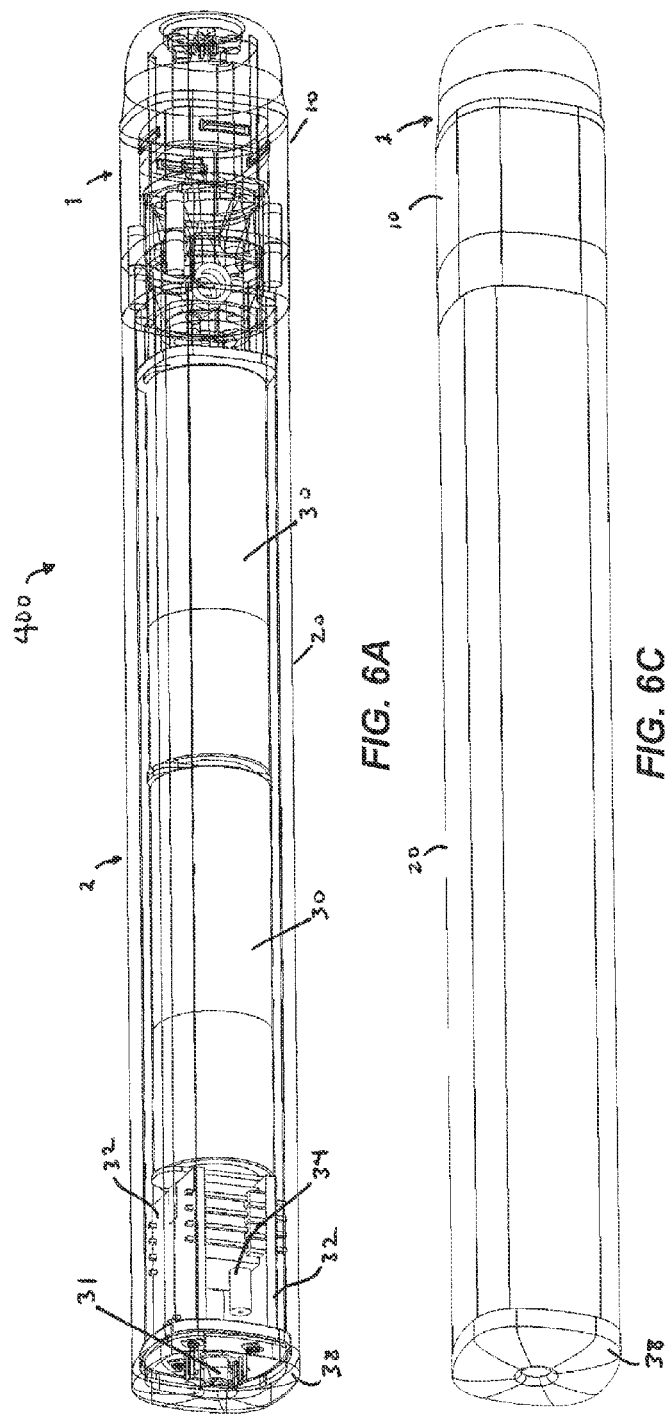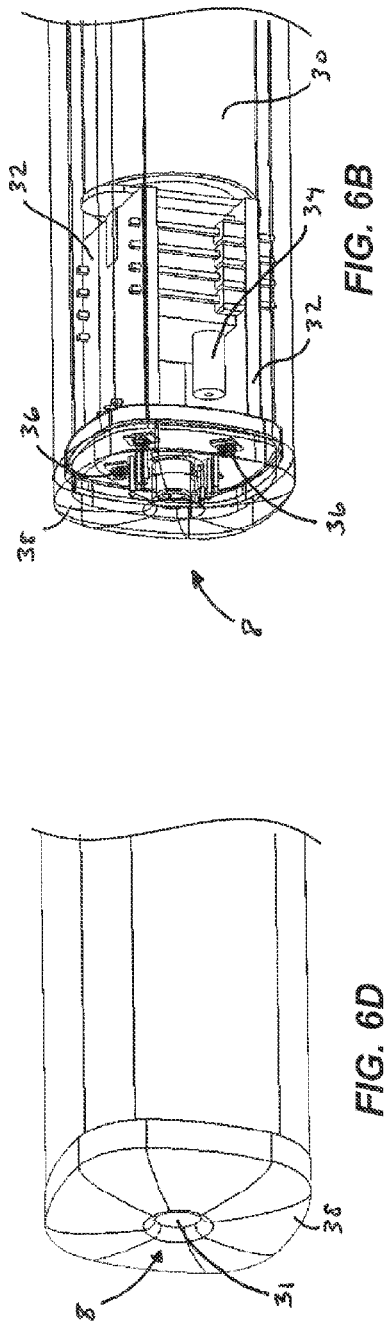

SECTION

DETAIL A

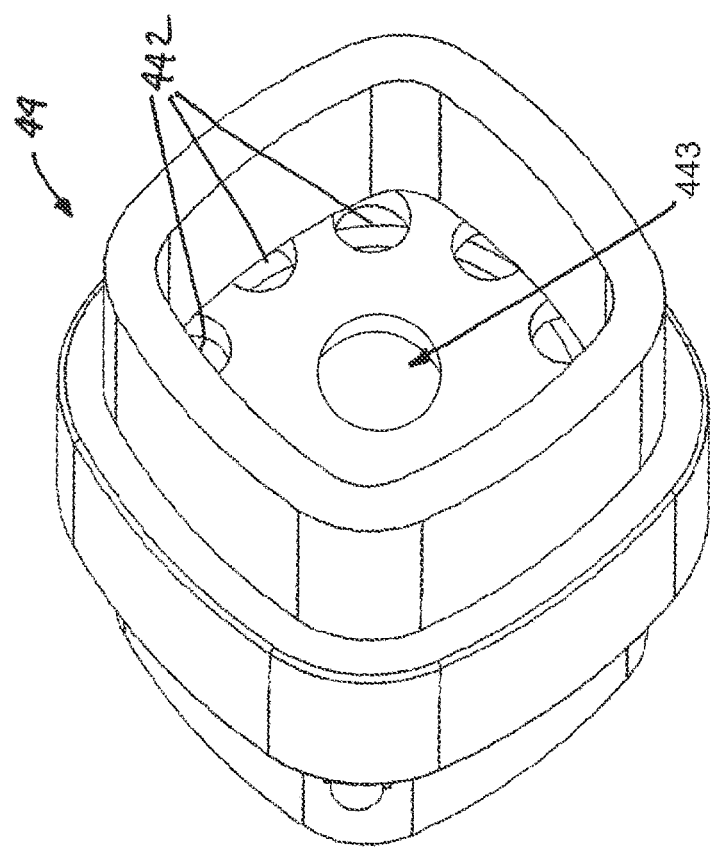
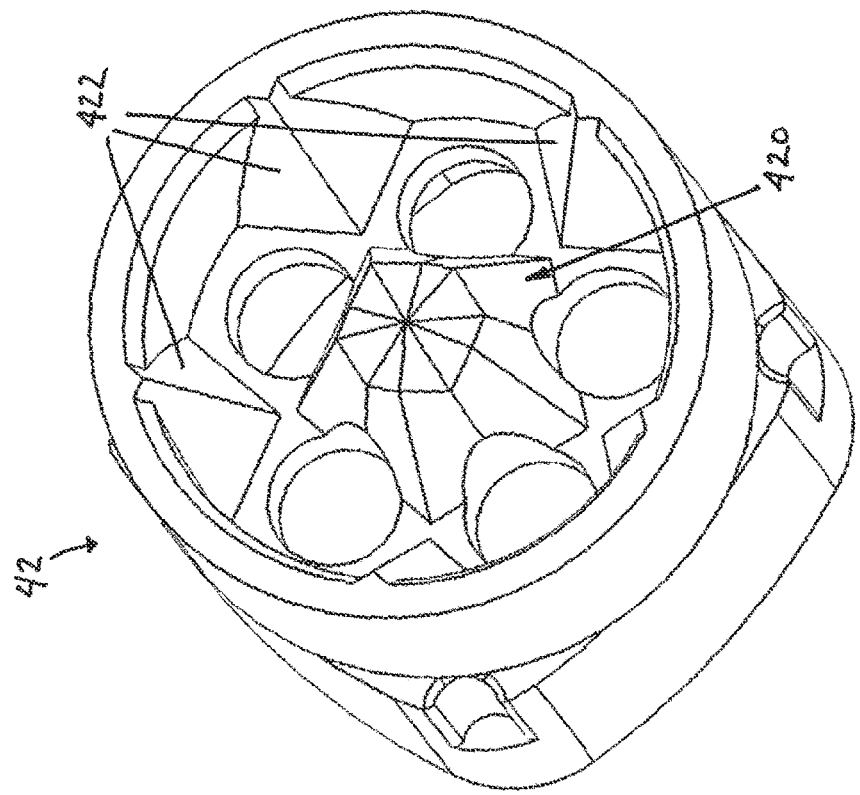
FIG. 10B
FIG. 10A

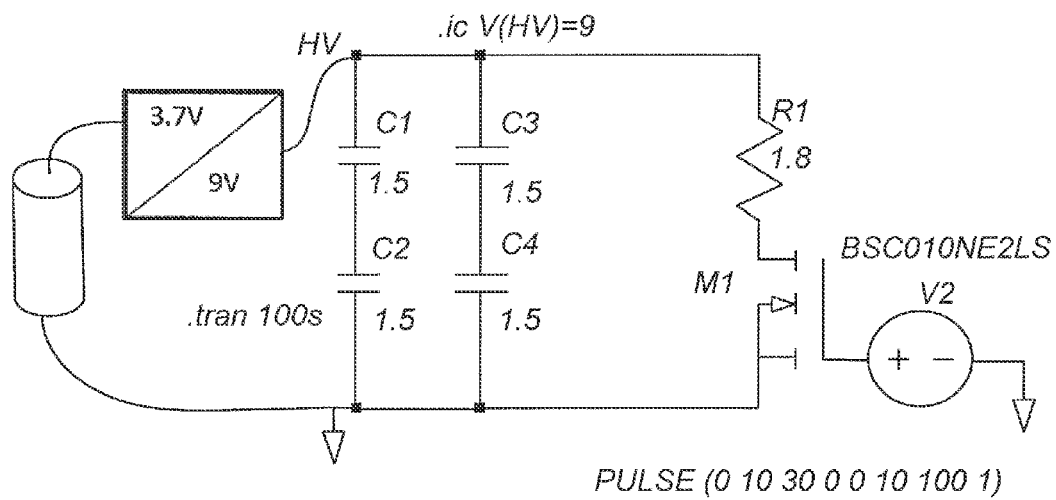
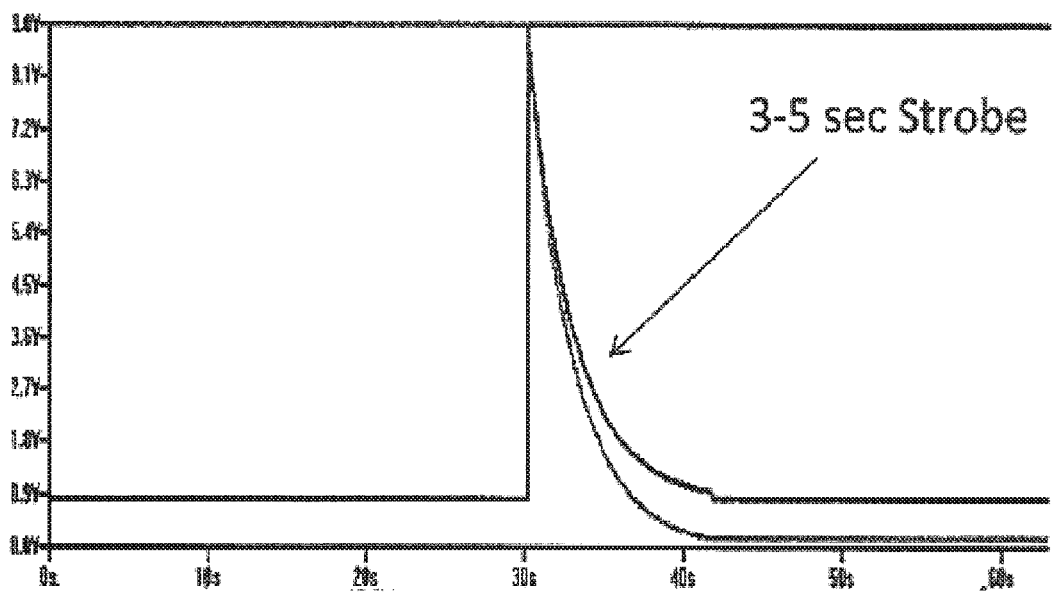
FIG. 12

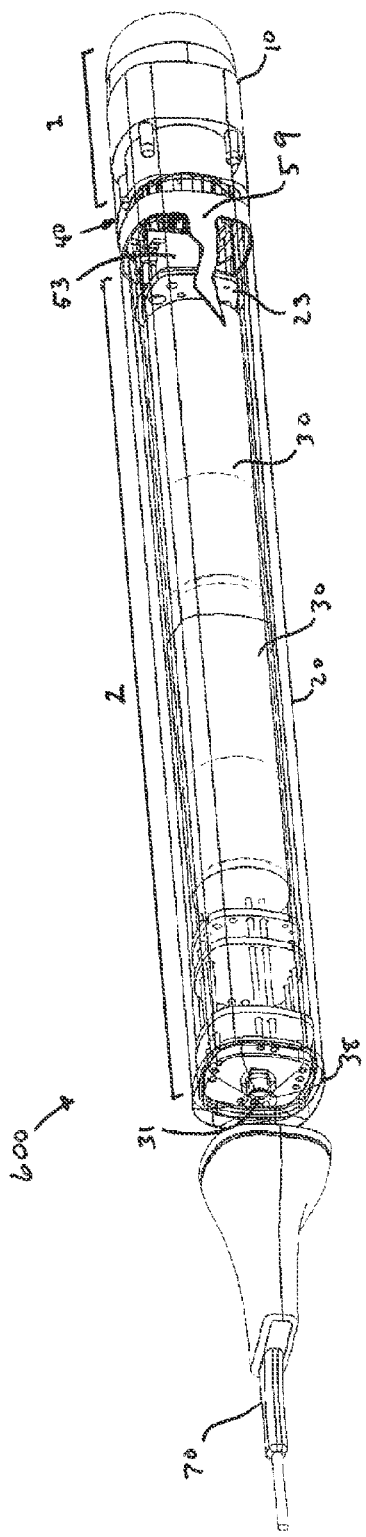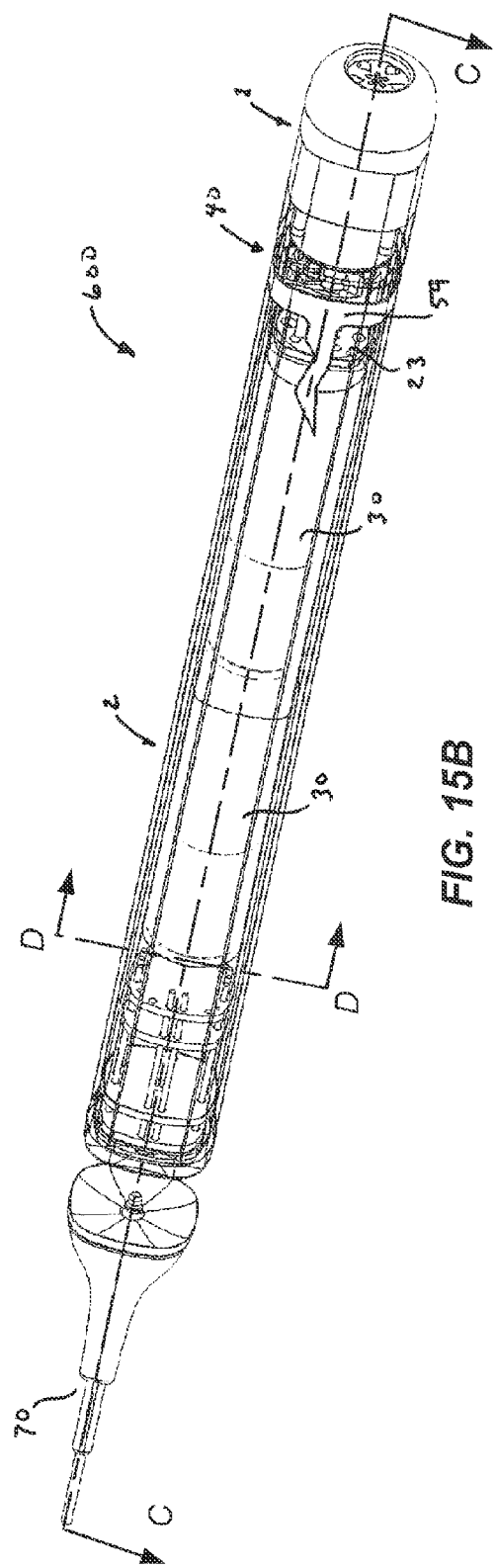
FIG. 15A
FIG. 15B

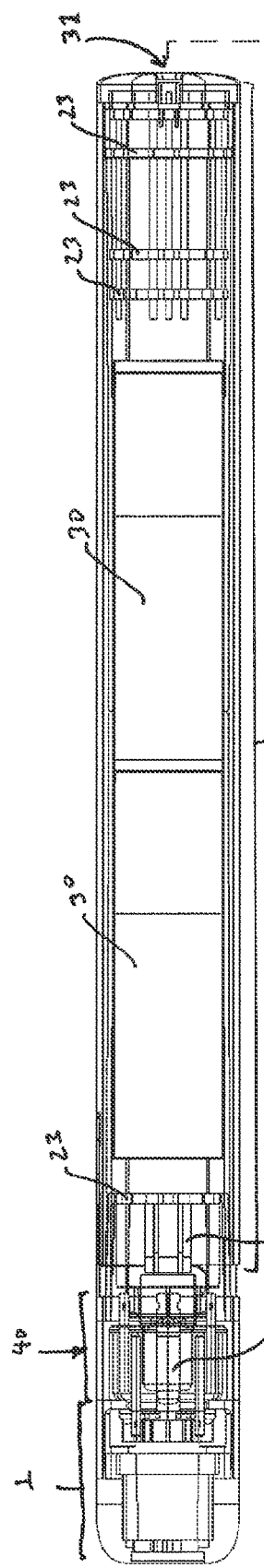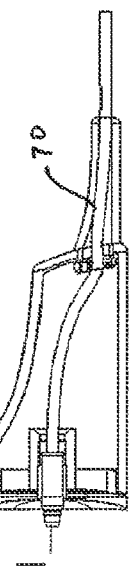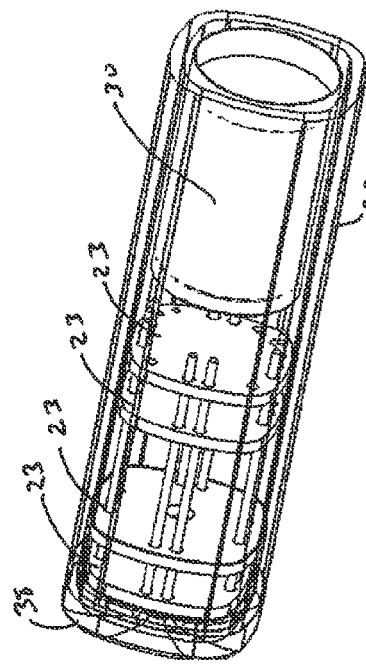
FIG. 15C SECTION C-C
FIG. 15D SECTION D-D
FIG. 15E

ELECTRONIC VAPORIZING DEVICE AND METHODS FOR USE

CROSS-REFERENCES TO RELATED APPLICATIONS

This application is a Non-Provisional Application of and claims priority to U.S. Provisional Application No. 61/609,813, filed on Mar. 12, 2012, the entire contents of which are incorporated herein by reference.

BACKGROUND OF THE INVENTION

The present invention generally relates to an electronic vaporizing device, and in particular to an electronic vaporizing device having improved functionality and increased capability.

Although various electronic smoking and vaporizing devices currently exist in the market, conventional devices have considerable drawbacks. For example, many conventional portable smoking and vaporizing devices have heating units that utilize chemical reactions to provide sufficiently rapid heating, for example a catalytic heater. A catalytic heater generates heat through a flameless catalytic reaction involving butane (or propane) and oxygen; the heat is generated by bringing the butane and oxygen from the air into contact with a platinum catalyst, which causes a chemical reaction in which butane and oxygen are converted into primarily carbon dioxide and water vapor during which heat is released. In order to start the reaction, the fuel and air mixture must be ignited by an external heat source, such as a spark or pilot light. Using chemical reactions to provide vaporizing heat has considerable shortcomings, which include frequent refilling of the butane source, inability to transport the devices (e.g. airplane travel), gaseous emissions from the butane reaction, the unpleasant scent associated with the chemical reaction, a slow heat up time due to the time required to transfer the heat to the heating element (e.g. a platinum element), and variability of operation, particularly at high altitudes. Additionally, a chemical reaction cannot typically be easily or readily stopped to allow for rapid cooling. Although the source of butane can be stopped, the reaction will generally continue until the butane already provided is spent; thus, heating units utilizing butane chemical reactions are not amenable to rapid heating or cooling, and include various drawbacks.

Many conventional electronic vaporizing devices that allow for vaporization of a liquid solution, use a wick to transfer the liquid solution, such as a propylene glycol/nicotine solution, from a capsule or cartridge onto a microheating element. Vaporizing the solution by directly contacting the heating element often severely reduces the life of the heating element so that such devices often require frequent replacement, so much so that some such devices employ a disposable "cartomizer" which combines the heater and nicotine capsule into one piece. Once the nicotine solution is used up, both the heater and capsule are thrown away. Other conventional devices use completely disposable units, in which both the cartomizer and battery power source are thrown away after use. Due to the difficulties associated with these configurations, such devices are prone to premature failure and often don't work particularly well even when functioning normally. Additionally, conventional electronic cigarette devices do not generally allow users to vaporize their own materials in addition to a liquid cartridge, only proprietary nicotine cartridges of questionable purity. Moreover, most such devices lack any indicator of when the nicotine capsule is exhausted so that user must determine for themselves when it is appropriate to change capsules.

Another considerable drawback of many conventional devices is power consumption. Although conventional vaporizers employ a number of mechanisms to heat matter, most are power intensive and must be plugged into a wall outlet during operation. Although portable vaporizers currently exist on the market, each has significant drawbacks. For example, non-portable vaporizers are generally limited to table tops, and require the user to grind their herbs before vaporization. Many such devices have long heat up times, anywhere from two to ten minutes, so that it is impracticable for a user to directly inhale the vapor through the device. Therefore, such devices often employ plastic tubing called "whips" or inflated plastic bags to deliver their vapor, which can be inconvenient and negatively impact the smoking experience particularly in a social setting. Additionally, conventional vaporizers often provide poor temperature control, frequently break, and operate inconsistently.

In view of the above noted difficulties associated with conventional smoking and vaporizing devices, there is a need for improved devices that address these drawbacks, as well as provide improved portability and increased heating efficiency, and that allow a user to select a variety of differing substances including both cellulose plant material and various pre-prepared substances for vaporization, while providing an enhanced "smoking" experience for the user.

BRIEF SUMMARY OF THE INVENTION

The present invention relates generally to electronic vaporizers, and more particularly to an electronic vaporizer having improved heating and/or vaporizing capability.

In an example embodiment, the device is a portable vaporizing device having an outer housing with an axial passageway extending therethrough that allows inhalation of air from a distal portion through a proximal portion of the device, the axial passageway including a receptacle for holding a substance to be vaporized, a portable power source, an inhalation sensor for detecting air flow through the axial passageway for sensing inhalation through the axial passageway, and a heating portion disposed within the axial passageway, the heating portion including a heating element, such as a nichrome wire or coil, bulb heater, metal screen heater, flat or thin film heater, ceramic heater, polyimide heater, aluminum heater, LED heater, radiative heater, or other heating element suitable for sufficiently heating the substance to be vaporized within the receptacle so as to vaporize the selected substance for inhalation by a user, or various combinations thereof. The heating element may be separate from the receptacle so as to heat the air and vaporize the selected substance through convection as air flows through the heating element or may be included within the receptacle or adjacent chamber. In some embodiments, the heating portion includes a reflector for reflecting radiation from the heating element so as to radiatively heat the air flowing through the passageway.

In certain aspects, the power source of an example vaporizing device is configured to energize the heating element in response to a determination of inhalation by a user using the inhalation sensor. The power source may be configured to determine and alter a power output to the heating element in response to an output from any or all of a thermistor, the inhalation sensor, and an elapsed time so as to provide a desired vaporization temperature. In certain aspects, the desired air flow temperature for vaporization is within a range from about 170° C. to 200° C. Preferably, the power source is configured to provide the desired vaporization temperature within less than three seconds of detection of inhalation. In certain embodiments, the power source supplied to the heating unit is less than 30 Watts, preferably within a range from about 15 to 25 Watts. In some embodiments, the power source is configured to energize the heating element according to a duty cycle and/or by heating upon detection of inhalation for 10 seconds or less.

In another aspect, an example device includes a rechargeable power source and includes a recharging port electrically coupled with the power source so as to recharge the power source when coupled with an external power source. In other embodiments, the power source may be removable or replaceable. An example embodiment further includes a distal light source electrically coupled with the power source, wherein the distal light source is configured to output light in response to a determination of inhalation using the inhalation sensor. Often, the distal light source is a variable illumination light source configured to vary illumination in response to an output from the inhalation sensor, so that the light output is proportionally related to the air flow through the sensor. The distal light source may include one or more LEDs of the same or differing colors, preferably four red LEDs and at least one green LED. In some embodiments, the distal light source is configured to provide an indicator of a state of the device, wherein the state of the device includes any or all of: a low level of power, a fully recharged state, a low level of substance to be vaporized, and a recharging state. The indicator may comprise a light output of differing color and/or a blinking light output.

In another aspect, an example device includes a grinder portion for grinding a cellulose based plant material selected by a user, such as any of a variety of tobacco blends selected by a user. The grinder portion may define a grinding cavity, wherein the grinding cavity is accessible by a user to allow relatively large particles and portions of cellulose based plant material to be placed within the grinding cavity. In certain embodiments, the receptacle for holding the selected substance includes the grinding cavity. The grinder portion may include a proximal and distal grinding portion, wherein the proximal and distal grinding portions are coupleable so that the, in combination, the proximal and distal grinding portions define the grinding cavity when coupled, each of the proximal and distal grinding portions including teeth extending into the grinding cavity when coupled, the proximal and distal grinding portions being separable from each other so as to allow a user to access and insert the selected substance within the grinding cavity. The proximal and distal grinder portions may be rotatable relative to each other so as to move the teeth of each portion in opposite directions when rotated to grind the solid substance when placed within the grinding cavity of the device.

In certain embodiments, the proximal and distal grinder portions each include an undulating surface, the undulating surface of the proximal portion interfaceable with the undulating surface of the distal grinder portion, the undulating surfaces translating rotational movement into axial movement so that when the portions are rotated relative to each other during grinding, engagement of one undulating surface against the other undulating surface causes axial back and forth movement of the grinder portions when the portions are coupled so as to facilitate break down of the substance to be vaporized when placed within the grinding cavity. Often, the proximal grinder portion includes one or more magnets interfaceable with one or more corresponding magnets in the distal grinder portions, configured so that when the magnets are interfaced, the undulating surfaces of each portion are interfaced, and when the magnets are separated, the undulating surfaces of each portion are separated. In certain embodiments, the portable power source is configured so as to energize the heating portion in response to sensed air flow by the inhalation sensor, wherein the sensed air flow corresponds to inhalation by a user. An example device may further include a cartridge containing a liquid vaporizing solution, gel, wax oil, solid brick of material, or some combination thereof for vaporizing the cartridge configured for insertion into the receptacle by a user. The cartridge, or an additional cartridge, may also include flavorings to flavor the inhaled product or colorings to color the exhaled vapor. In some embodiments, the device includes a separate receptacle for receiving the cartridge, whereas in other embodiments, the cartridge may be placed directly into the grinding cavity.

In another aspect, example methods are provided for vaporizing a substance selected by a user. An example method includes determining inhalation by a user through the device with a pressure sensor disposed within an air passageway extending through the device; determining a power output from a portable power supply in the device to a heating portion of the device so as to provide a desired vaporization temperature to vaporize the substance by the user within the device; energizing the heating portion with the determined power output; heating the air flowing through the heating portion to the desired vaporization temperature using convection and radiative heating within less than three seconds of determining inhalation, or heating the selected substance with the heating portion to the desired vaporization temperature using conduction and radiative heating within less than three seconds of determining inhalation. Example methods may include any or all of the aspects described herein in accordance with embodiments of the present invention.

BRIEF DESCRIPTION OF THE DRAWINGS

Although the following figures depict various examples of the invention, the invention is not limited to the examples depicted in the figures.

FIGS. 1A-1B illustrate perspective views of an electronic vaporizing device in accordance with embodiments of the invention. FIG. 1A illustrates a perspective of the device from a distal viewpoint and FIG. 1B illustrates a perspective from a proximal viewpoint.

FIGS. 2A-2B illustrates cross-sectional views of the electronic vaporizing device in FIG. 1A. FIG. 2A illustrates a cross-sectional view along section A-A of FIG. 1B, and FIG. 2B illustrates a cross-sectional view along section B-B of FIG. 1B.

FIGS. 3A-3D illustrates an alternate perspective view and detail views of the device and/or the components of the device in FIG. 1A. FIG. 3A illustrates a perspective from a side view with the outer housing shown transparent for visibility of the interior components. FIG. 3B illustrates a detail of the proximal portion of the device shown in FIG. 3A. FIG. 3C shows a detail view of the proximal portion shown in FIG. 3A with the mouthpiece removed. FIG. 3D shows a detail view of the mouthpiece of the device in FIG. 3A.

FIG. 4A illustrates the activation switch before activation by inhalation and FIG. 4B illustrates the activation switch after activation by inhalation.

FIG. 5A illustrates a perspective from a side view with the outer housing shown transparent for visibility of the interior components. FIG. 5B illustrates a detail exploded view of the distal-most portion of the device in FIG. 5A.

FIGS. 6A-6D illustrate perspective and detail views of another example vaporizing device. FIG. 6A illustrates a perspective of the device from a side view with the outer housing shown transparent for visibility of the interior components. FIG. 6B shows a detail view of the distal-most portion of the device shown in FIG. 6A. FIG. 6C shows the perspective side view of FIG. 6A with the outer housing shown solid. FIG. 6D shows a detail view of the distal-most portion of the device shown in FIG. 6C.

FIG. 8A illustrates a side view of the heating unit shown in FIG. 7. FIG. 8B illustrates a top view of the heating unit shown in FIG. 7. FIG. 8C illustrates a cross-sectional view along section E-E in FIG. 8B. FIG. 8D shows a detail view of detail A shown in FIG. 8C.

FIG. 9A illustrates the components of the grinder disassembled and FIG. 9B shows the grinder components assembled.

FIGS. 10A-10B illustrate components of an example grinder for use in a device. FIG. 10A illustrates a proximal grinder portion and FIG. 10B illustrates a corresponding distal grinder portion.

FIG. 11A illustrates an assembled cartridge loaded with a substance to be vaporized with the device. FIG. 11B illustrates an exploded perspective view of the components of the loaded cartridge.

FIG. 12 illustrates a circuit diagram and operational graph of four ultra-capacitors for use as a power source in an example device.

FIG. 13A illustrates a perspective from a side view of the device and FIG. 13B illustrates an exploded view of the side view perspective shown in FIG. 13A.

FIG. 14A shows a perspective from a side view of the vaporizing device being recharged through a USB connector cable. FIG. 14B shows a detail view of the distal portion of the vaporizing device in FIG. 14A with the endcap removed and the outer housing shown transparent for visibility of the USB recharging receptacle. FIG. 14C shows a perspective from a distal view of the vaporizing device being recharged through a USB connector cable.

FIGS. 15A-15E illustrate an example vaporizing device having a bulb heater and a removable cleaning tool and a recharging cord in accordance with embodiments, associated cross-section views and a detail view of the cleaning tool, respectively. FIG. 15A shows a perspective from a distal view with the outer housing shown transparent for visibility of the interior components. FIG. 15B shows a perspective from a proximal view with the outer housing shown transparent for visibility of the interior components. FIG. 15C shows a cross-sectional view of the vaporizing device and recharging cord along section C-C of FIG. 15B. FIG. 15D shows a cross-sectional view along section D-D of FIG. 15B. FIG. 15E shows a detail view of the cleaning tool of the device shown in FIG. 15A.

FIG. 16A illustrates a detail of a perspective side view of the proximal portion of the device of FIG. 15A with the distal grinder portion removed for visibility of the bulb heater and bulb chamber. FIG. 16B illustrates a detail perspective view of the bulb heater shown in FIG. 16A.

FIG. 17 illustrates an example method of vaporizing a selected substance in a vaporizing device. FIG. 18 illustrates an example method of selecting, grinding and vaporizing a substance using a vaporizing device. FIG. 19 illustrates an example method of controlling power during vaporizing of a selected substance in a vaporizing device.

DETAILED DESCRIPTION OF THE INVENTION

Figure 3C:
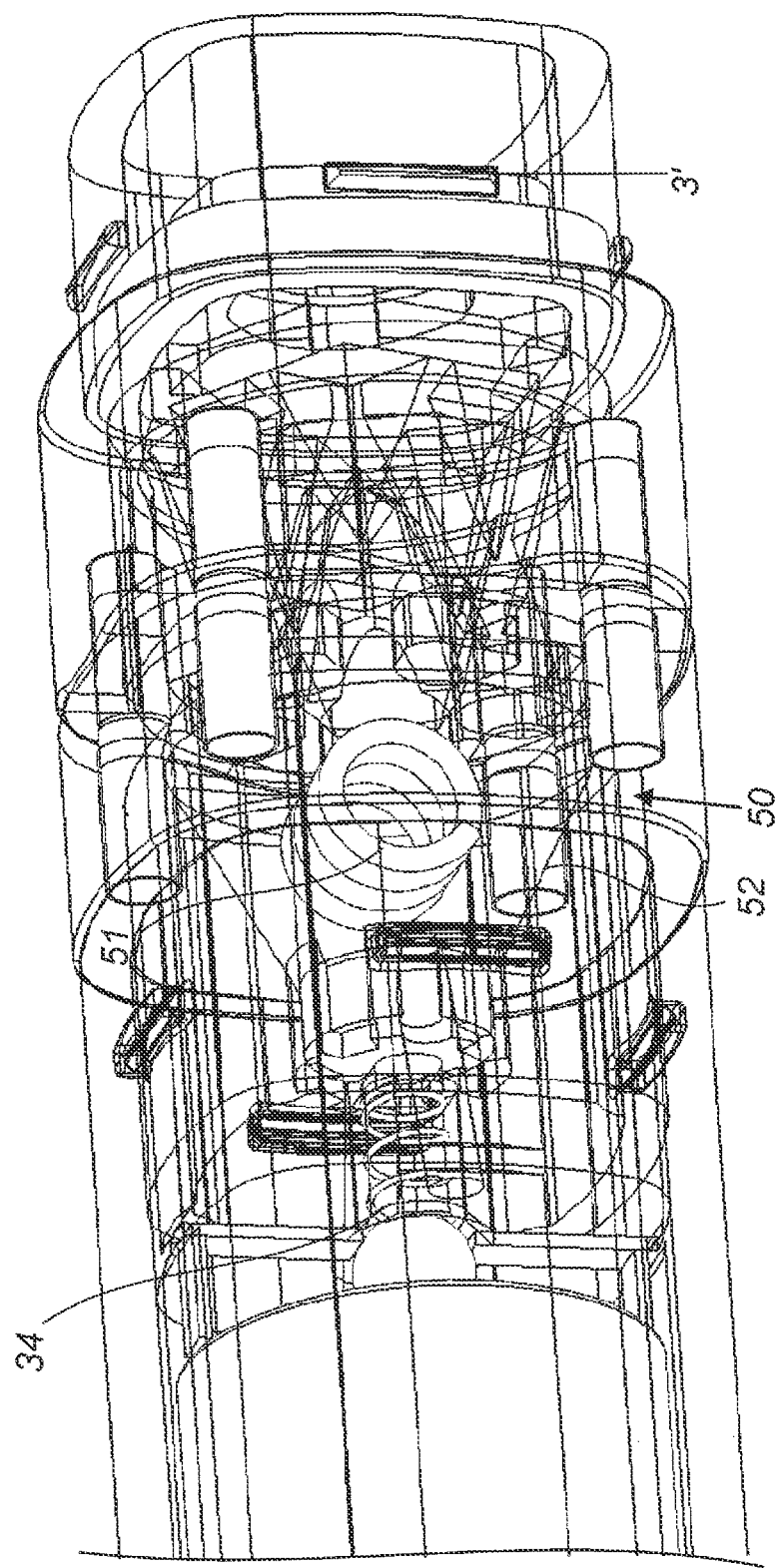

This invention relates generally to electronic vaporizing devices, and more particularly to a portable electronic vaporizing device having improved functionality and additional capabilities, as well as methods of vaporization and methods of use.

In an example embodiment, the invention provides a portable electronic vaporizing device having an outer shell housing internal components that facilitate heating and vaporizing of the selected substance disposed within for inhalation by a user. The device may be configured as a portable handheld device having an internal power source to allow for use over an extended period of time and/or use on multiple occasions without requiring recharging or replacement of the power source. The device is further configured to provide improved functionality, increased capabilities, and an enhanced "smoking" (more accurately inhalation of vapor) experience when compared to conventional electronic smoking and vaporizing devices. In certain aspects, the device allows for heating and vaporization of any of a variety of substances selected by a user for inhalation, preferably using various combinations of convection, radiation and conduction so as to more efficiently heat and vaporize the selected substance while providing a reduced lag time in vaporizing the material, thereby allowing for an enhanced "smoking" experience, similar to actual traditional smoking using combustion without the associated drawbacks.

In general, vaporizing a substance for inhalation provides significant benefits over traditional methods of smoking or burning a substance through combustion. In traditional cigarette or cigar smoking, tobacco leaves are burned through combustion to volatilize the active ingredients (e.g. nicotine) found naturally within the leaves. Although this method allowed a user to inhale the active ingredients, burning of a substance through combustion is a chemical process which also produces a variety of harmful and irritating toxins, most notably carbon monoxide and tar. During inhalation in traditional smoking using combustion, the tobacco leaves are heated to a temperature of about 600° C. to 900° C. during which many of the harmful toxins noted above are volatilized and inhaled by a user, resulting in many of the well-known harmful health effects associated with smoking. In contrast, vaporization allows for heating of a selected substance, such as tobacco, to a substantially lower temperature that volatilizes the active ingredients within a vapor suitable for inhalation, while avoiding volatilization of harmful tarry substances and the production of carbon monoxide associated with combustion. Additionally, vaporization may allow more of the active ingredients to be inhaled, since vaporization generally delivers more than half of the active ingredients within a substance, while in traditional smoking about ⅔ of the active ingredients are destroyed or incinerated during combustion. Even without using combustion, however, overheating of the substance will still volatilize and deliver harmful toxins (e.g. tar) to the user. Thus, vaporization at controlled temperatures allows a user to inhale the active ingredients of various selected substances without many of the harmful side-effects associated with traditional smoking using combustion.

Vaporizing a selected substance using convection and radiation, in accordance with various embodiments of the present invention, has significant advantages over vaporization methods used in many conventional devices. Often conventional devices utilize conduction, either as a primary or a secondary heating method, which presents significant drawbacks. Conduction can cause uneven heat distributions, undesirable overheating of the substance to be vaporized, and/or "caking" or "baking" of the substance on the conductive material that often results in build-up of the "caked" substance requiring cleaning or replacement of the heating component. In many devices relying on conduction heating, difficulties in controlling heating of the substance results in poor, or inconsistent vaporization of a substance or overheating of the substance, which may cause inadequate vaporization or inhalation of the harmful toxins typically associated with smoking using combustion methods, respectively. Additionally, since the heat associated with many conventional conduction heating devices is often less uniform, such devices may be less efficient and may produce a vapor of unpredictable potency. In many such conduction models, the vapor gathers more slowly in the device, such that direct inhalation through such a device is unlikely to provide the level of vaporization desired. By utilizing a combination of different heating mechanisms, such as convection, radiation and conduction, the device allows for more consistent and controlled vaporization of the selected substance so as to enhance the benefits of vaporization. These advantages of vaporization can be further enhanced by providing optimum temperature ranges of vaporization for a particular selected substance, and by controlling the uniformity of heating through the substance so as to avoid overheating of the substance.

In an example embodiment, the device allows for vaporizing of a variety of substances selected by a user to be vaporized, from relatively large pieces of intact cellulose-based plant materials to various forms of pre-prepared substances. Cellulose-based plant material may include a variety of plant materials having active ingredients, such as a personalized blend of tobacco, lavender, sage, thyme and/or various herbs or plant materials. The pre-prepared substance may include a substance having active ingredients in a variety of forms, including liquid or gel solutions, waxes, oils, powders and solid bricks of material. In certain embodiments, the device includes a grinder incorporated into the device so as to allow a user to grind intact pieces of cellulose-based plant materials into a form more suitable and amenable to vaporization of the active ingredients within. In some embodiments, the device includes a cartridge in which the pre-prepared substance may be disposed, the cartridge being placed in a cartridge receptacle or within the grinding cavity itself.

In an example embodiment, the invention provides an electronic vaporizing device having an outer shell housing internal components that facilitate heating and vaporizing of the selected substance disposed within for inhalation by a user. In various embodiments, the device is a portable handheld device having an internal power source to allow for use over an extended period of time and/or use on multiple occasions without requiring recharging or replacement of the power source. The device is further configured to provide improved functionality, increased capabilities, and an enhanced "smoking" or vaporizing experience when compared to conventional electronic smoking and/or vaporizing devices. The device allows for heating and vaporization of the selected substance disposed within upon inhalation by a user, preferably using combinations of convection, radiation and conduction so as to more efficiently heat and vaporize the selected substance while providing a reduced lag time in vaporizing the material, thereby allowing for an enhanced vaporizing experience, similar to actual traditional smoking without the associated drawbacks. In an example embodiment, the device allows for vaporization of a variety of substances selected by a user, from cellulose based plant material to pre-prepared liquid, gel, wax, oil, or solid bricks of the substance. The device may include a grinder incorporated into the device so as to allow a user to grind and vaporize any of a variety of cellulose based substances according to a user's individual preferences, such as tobacco leaves or a personalized blend of tobacco, herbs, and/or smoking aromatics.

In an example embodiment, the invention also provides for improved functionality and aesthetics to provide a more realistic satisfying "smoking" or vaporizing experience for a user, being configured to resemble the general appearance of a cigarette or cigar including the lit end of a cigar during traditional smoking. Often, inhaling active ingredients vaporized within a vaporizing device is still referred to as "smoking" despite no smoke being produced as in traditional smoking using combustion. In certain embodiments, the device includes a main body housing having an air passageway therethrough, a distal light source within the main body to simulate the burning end of a cigar, a power source, a heating unit, an internal grinding unit for grinding a selected substance, an air flow sensor, associated circuitry, electronics and memory for activating and controlling the device, as well as various filters and screens for isolating internal portions of the device and for filtering the vapor for inhalation. In some embodiments, one or more metal screens may be included in the mouthpiece to filter large particulates in the inhalation stream and to provide a heat sink to cool the heated air before inhalation into a user's mouth. In some embodiments, the device may include removable and/or interchangeable mouthpieces in varying sizes, colors, or flavors so that a user could change out the mouthpiece according to a user's preference. Some embodiments, include a cleaning tool or pick for cleaning particles accumulated within the filters or screens. The cleaning tool may be a pointed metal tool or brush-like tool that is removably coupled or stored within the device. In certain embodiments, the device includes an optional cartridge that allows a user to vaporize a pre-prepared substance having active ingredients, which may be in a variety of differing forms, such as a liquid solution, gel, wax, oil, powder, or solid brick of material. Often the device includes a connector to allow for recharging of the internal power source. In example embodiments, the above components are configured so as to provide a highly portable device that provides improved efficiency in heating, improved portability and battery life, as well as an enhanced vaporizing experience.

In certain embodiments, the device includes a power source using one or more batteries, such as rechargeable and/or replaceable batteries, such as 18650 high discharge lithium ion batteries. Generally, the device includes two rechargeable batteries placed in series within the main body, which can be recharged by attaching the device to a power source with a power cord, such as a connector pin or USB device. In various embodiments, the device can be used for an extended period of time without recharging or replacing the batteries, such as a typical "smoking" or vaporizing session lasting an hour or more, typically two or more hours. In a typical session, a user inhales at a flow rate of about 0.125 L/s for about 5 seconds or less at periodic intervals during the session, for example about one to ten inhalations per minute. Generally, the rate of usage (volumetric flow over time) is inversely related to the duration for which the device can be used without recharging and/or replacing the power source. For example, the period of time the device may be used on a single charge may be longer during a vaporizing session with a relatively low rate of usage, such as one inhalation per minute, than in a session having a relatively high rate of usage, such as seven inhalations per minute.

In some embodiments, the device includes a power source activation switch and/or firmware that controls the power so as to conserve power and improve portability of the device, allowing the device to be used for longer periods of time or at multiple sessions over a period of days, weeks, and/or months on a single charge. In various embodiments, the power source is configured so as to minimize and/or terminate power consumption when the device is not in use (e.g. when air is not being inhaled through the device), thereby increasing the ease of use and portability of the device. In an example embodiment, the inactive device draws about 0.5 mA or less, such that the power source maintains a charge sufficient for operation for about 25 to 30 days.

In an example embodiment, the device includes an outer shell housing constructed to simulate a cigar in its general shape and appearance, although it is appreciated that the device could be designed in a variety of differing shapes, including but not limited to a cigarette, pipe or any other such shape suitable for a handheld portable device. In certain embodiments, the device allows for improved ease of use by utilizing an inhalation sensor. In response to airflow sensed by the inhalation sensor, the heating unit is energized so as to heat and vaporize the selected substance therein. The device may also be configured so that in response to inhalation, the device also activates a distal light source, such as one or more LEDs, to simulate the lit tip of a cigar. The device may include firmware and/or circuitry that varies the light output of the distal light source in proportion to the level of airflow drawn through the device. For example, inhaling at a low flow rate would activate one LED, while inhaling at a higher flow rate would activate four LEDs so as to more closely simulate an actual lit tip of a cigar. The distal light source may also be used to indicate various states of the device, such as a low level of the substance within the cartridge, a lower power source, or an indication that the device is charging or has been fully charged. In certain embodiments, the distal light source is disposed within the distal end of the main body protected under a removable clear or translucent lens tip.

In certain embodiments, the device is configured to heat and vaporize both cellulose based plant matter and a preprepared mixture or solution. The device may include a cavity for inserting a capsule or cartridge containing the material to be vaporized, which may include any of a liquid or gel solution, wax, oil, or a mixture such as a powder or solid brick of material. Alternatively, the device may be configured so that a user can insert or refill the material to be vaporized directly into the device. The cavity may be incorporated into the grinder portion, may be separate therefrom, or may be included in a separate removable portion of the device that can be attached to the device (or alternatively, could replace the grinder portion).

In an example embodiment, the device includes a proximal portion and a distal portion, between which the grinding cavity is defined when the portions are assembled. The grinder is configured so that a user can insert a selected substance into at least one of the portions, and after assembling the portion, can activate the grinder so as to grind the solid substance in preparation for vaporizing. In certain embodiments, the device includes mesh screens, porous membranes or members having a plurality of small holes so as to isolate the grinding cavity from adjacent portions of the device. The grinder is activated by rotating the proximal portion relative to the distal portion, or vice versa, so as to move and rotate internal burrs of the grinding portion past one another so as to tear and grind the solid substance into minute particles suitable for vaporizing. Optionally, the grinder may be configured, such as by use of interfacing ramps or undulating portions, to translate rotational movement into axial movement thereby providing a mashing movement of the burrs to further facilitate grinding of the solid substance.

Example embodiments of the device, as well as various aspects and methods associated therewith, are illustrated in FIGS. 1A-19, and are described in more detail as follows:

I. Main Body Housing

In an example embodiment, such as shown in FIGS. 1A-1B, the device includes a main body 2 having a main body housing 20 that encases the internal components, such as the power source (e.g. batteries), a USB receptacle for recharging, a distal light source or LED, the heating unit, and at least a portion of a grinding chamber (the remaining portion often being attached to a removable portion or to a proximal portion having a mouthpiece). The main body housing is fabricated from a high-temperature polymer that is relatively light while providing thermal insulation, such as poly p-phenylene sulfide, which can withstand the high temperatures within during use, as well as provide insulative properties. This aspect is particularly advantageous since insulating the heating portion minimizes thermal losses through the housing, thereby reducing the amount of energy needed to heat the selected substance within and increasing overall efficiency and battery life. This feature also improves comfort for the user, since the insulative properties of the material prevents the housing from overheating, which is particularly important since the user holds outer housing 20 in their hands during vaporizing with the device. It is appreciated, however, that these insulative advantages may be achieved with a high temperature plastic or other thermally insulating material of the grinder portion or chamber such that the main housing may be fabricated from a wide variety of materials, including metals, such as aluminum or stainless steel or other suitable metals.

In certain embodiments, the device has a proximal mouthpiece portion 1, which includes a housing 10, to be place in the user's mouth. The housing 10 may be fabricated from the same or different materials than the main body housing 20. In some embodiments, the outer housing 10 and 20 are coated with paint, or a metallic or glossy layer, often for aesthetic purposes. The outer shells may also be constructed in a variety of shapes, although usually each of the outer housing 10 and 20 are fabricated in a roughly cylindrical shape, preferably in a square prismatic shape with rounded corners, as shown in FIGS. 1A and 2B, although various different shapes could be used in accordance with the principles of the present invention.

As shown in FIGS. 1A-1B, the main body housing 20 is elongated having a non-circular cross-section, such as a square with rounded corners. As shown in the cross-section of FIG. 2B, a main body housing having a non-circular cross-sectional shape is advantageous as it allows sufficient space for the power source 30 (e.g. cylindrical batteries) within defining air passageways 6 outside the batteries to allow flow of air through the device. Although a square shape with rounded corners is depicted, it is appreciated that various non-circular shapes could be used, such a triangular shape, an octagonal shape, etc. Additionally, it is appreciated that the main body housing could be constructed with a circular cross-section larger than the battery so as to allow sufficient air flow therethrough.

In an example embodiment, the main body housing 20 has in inner cross-sectional area of about 150-650 mm$^2$, preferably about 170-550 mm$^2$, or even more preferably about 170-450 mm$^2$, sufficiently large enough to allow sufficient air flow through the main body housing 20 upon inhalation so as to provide a satisfying inhalation, yet small enough to limit air flow therethrough to provide improved efficiency and to allow for increased ease of use and portability of the device. The cross-section of the main body housing 20 is a square by about 15 mm by 15 mm. In certain embodiments, the length of the device is about 150 to 300 mm long, such as about 230 mm long so as to provide sufficient space for the power source, air intake, heating portion, grinder, mouthpiece, inhalation sensor and associated electronics. Often, the heating portion is disposed within the device so that there is a distance between the heating portion and the opening of the mouthpiece to be placed within the user's mouth of about 20 mm to 60 mm, such as about 40 mm so as to allow for adequate cooling of the heated air before reaching the user's mouth. These dimensions are advantageous in allowing suitable airflow to allow for rapid inhalation detection through the device, improved efficiency in heating, and adequate cooling of the heated vapor for inhalation by the user. In certain embodiments, the air intake 8 is provided at or near the distal lens tip 38, such as through spaces 8 between the lens tip 38 and the distal opening of the device or through a central air passageway 8 (such as shown in FIGS. 6A-6D). This configuration is advantageous as it allow the air intake to be sufficiently far from where a user's hand grasps the outer housing 20 of the main body, so as to prevent inadvertent blockage of the air intakes by the user when holding the device.

II. Heating Unit

In an example embodiment, such as that shown in FIG. 3B, the device includes a heating unit comprising a heating element 51, such as a coil, and a reflector 52, distal of the coil so as to reflect and direct radiant heat so as to increase the efficiency of heating the air drawn through the device. The heating element may be a Nickel Chromium alloy wire, which may be miniaturized and optimized for maximum surface area and minimized mass, or may be a heater bulb, such as a Tungsten filament in quartz bulb. These configurations allow relatively high energy dissipation per unit time with relatively low energy input to achieve a desired operating temperature, when compared to conventional devices. The heating unit is designed to facilitate a rapid heat up, such as less than 5 seconds and more preferably less than 3 seconds, as well as rapid cool down. In the example embodiment of FIG. 3B, the heating unit is a micro-convection heater that rapidly dissipates heat into the air passing over and through it and includes a sculpted reflector 52 distal of the heating element to reflect heat, increasing heating efficiency and further shortening lag time in heating the air to a temperature suitable for vaporization of the selected substance.

In certain embodiments, the heating unit includes a ceramic component, such as a PTC ceramic, which has a positive thermal coefficient of resistance. Most ceramics have a negative coefficient, while most metals have a positive coefficient. While metals do become slightly more resistant at higher temperatures, this class of ceramics (for example, barium titanate and lead titanate composites) has a highly nonlinear thermal response, so that it becomes extremely resistant above a composition-dependent threshold temperature. Advantageously, this aspect of the material can be useful as a thermostat, since the current passes when it is cool, and does not when it is hot. In some embodiments, the heating unit includes a small flat disc of porous ceramic that is coated via chemical deposition with a thin (micron scale) coating of metal, the metal coating permeating the interior porous structure turning the ceramic into a honeycomb like heater with the entire interior surface acting to emit heat. In another aspect, the heating unit may include a flexible thin film heater, such as a polyimide heater, in which a metal lead is placed within a thermally conductive polymer film.

In certain aspects, the device heats the air sufficiently to a desired temperature to vaporize the selected substance within a few seconds of inhalation, preferably about 3 seconds or less, even more preferably about 2.5 seconds or less. In an example embodiment, the device utilizes a portable power source and a heating unit, such as any of those described above, to provide rapid heating of about 3 seconds or less by utilizing convection, radiation, conduction, or a combination thereof. This feature is advantageous as it allows the substance to be vaporized during inhalation by a user from a portable device, whereas devices taking longer to vaporize would not be conducive to directly inhaling from the device and conventional devices providing such rapid heating may consume too much power to be used with a portable power source such as a battery. In certain aspects, the heating unit is configured to have a sufficiently low thermal mass and a relatively high surface area so as to facilitate rapid heating to a temperature sufficient to vaporize the selected substance, thereby reducing the lag time to vaporization from initial inhalation with the device. The relatively high surface area allows heat to readily transfer to air or vaporizable substance, while the design breaks the air flow, creating turbulent flow and dissipating the distributed heat more evenly and more quickly. The design is further advantageous as it can operate within a confined space with air passing through it along only one access, such as in a cigar shaped housing as shown in many of the embodiments described herein. In some embodiments, the heating unit may include the use of ultra capacitors to further supplement the heating capability and increase heating efficiency. Aspects of using ultra-capacitors as a heating source are illustrated in FIG. 12. The heating unit may be configured so as to inhibit contact between the heating element and the selected substance (e.g. content of the grinder or the cartridge), such as by separating the grinder cavity from the heating unit with a fine metal screen or a filter. Although in other embodiments, the heating element may contact the selected substance so as to heat by conduction, convection and radiation. In such an embodiment, periodic movement of the grinder during use overcomes the uneven heating often associated with conductive heating in conventional devices. Thus, by combining various different mechanisms for heating along with a means for redistributing and recirculating the selected substance, the device provides more even consistent heating and vaporization. Thus, the grinder noted above may also function as a recirculator for a substance which has already been sufficiently ground to facilitate even heating and improved vaporization with the device. This feature allows for cleaner vapor and more efficient vaporization than conduction heating often used in conventional devices.

III. Distal Lens Tip and LEDs

Figure 5A:
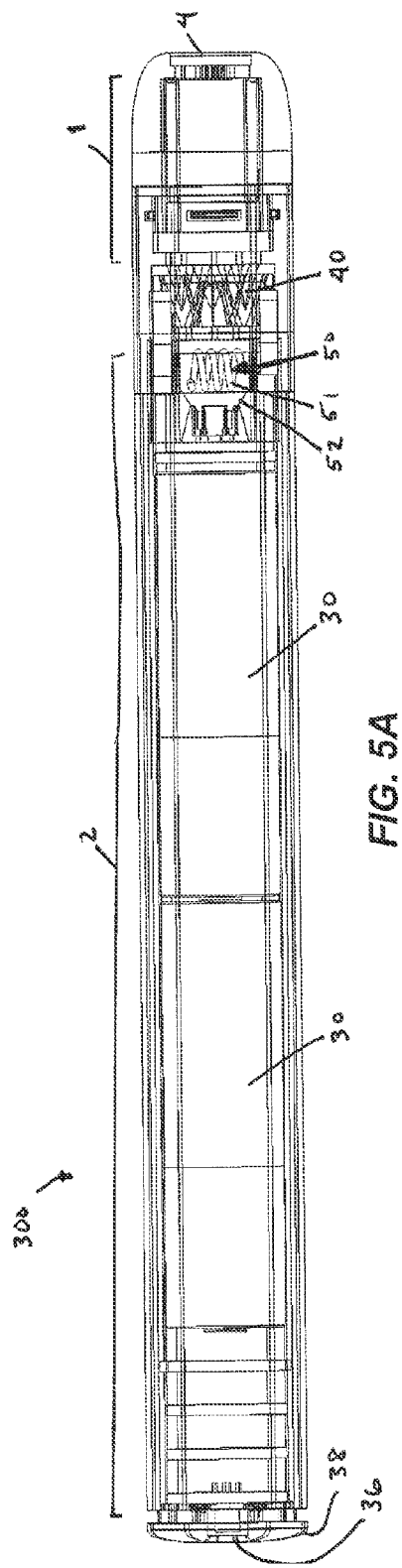
FIGS. 5A-5B illustrate a perspective and detail view, respectively, of another example vaporizing device.
Figure 5B:
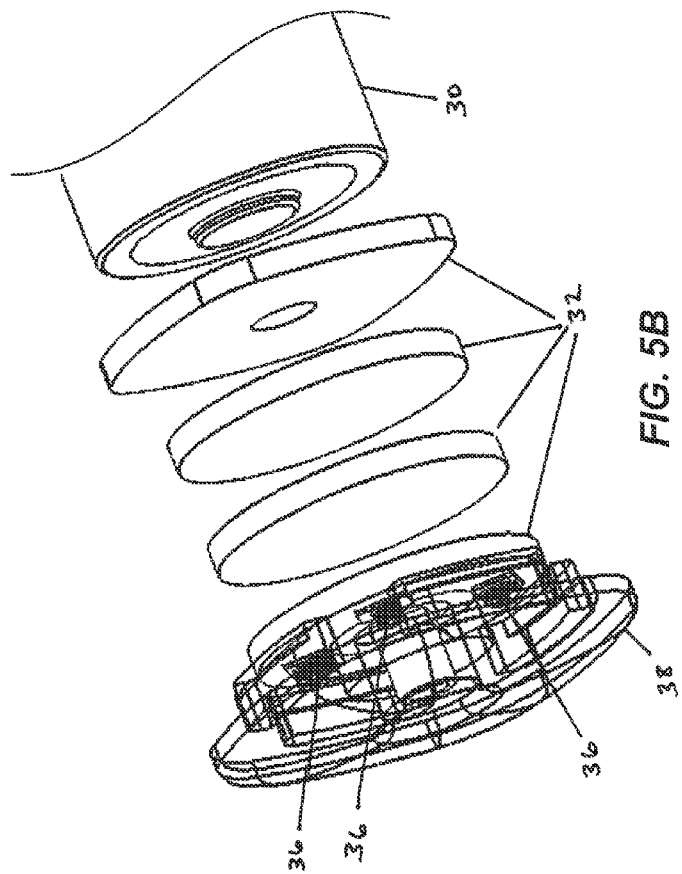

In an example embodiment, such as shown in FIGS. 5A-5B, the device 300 includes a distal light source 36, such as one or more LEDs mounted on a printed circuit board 32 situated behind the lens tip. The LEDs may be configured so as to fade up and down so as to vary in illumination intensity in proportion to an air flow velocity through the device so as to simulate the glowing tip of a cigar so that when the user inhales faster, the LEDs glow brighter, just as the lit tip of a cigar flares up with a quick inhalation. As described above, the LEDs may also signal or provide an indication of various states of the device to a user, such as a low battery, fully charged states, active charging, error/damage, or a low cartridge level. Differing states may be indicated in a variety of ways, including but not limited to use of LEDs of differing color, blinking patterns, or other such manner. For example, a green LED could be used to indicate the device is charging and a blinking LED may be used to indicate the device power is in need of recharging.

Figure 14A:
FIGS. 14A-14C illustrates an example vaporizing device with a USB plug for recharging.

In an example embodiment, such as that shown in FIG. 2A, the device includes a distal lens tip 38 that covers the distal end of the main body 2 of the device. The distal lens tip 38 may be a translucent or clear end cap that covers a distal light source 36, such as one or more LEDs disposed near the distal end of the device, such as four red LEDs. The portion of the end cap that interfaces with the distal end of the distal portion may include gaps or openings 8 to allow airflow into the passageway extending through the main body upon inhalation by a user. In certain embodiments, the distal end also includes a connector receptacle or port 31 (as shown in FIGS. 14A and 15A for example), such as for use with a recharging connector, such as a USB connector or a connector pin, to facilitate recharging of the power source therein. The distal end cap 38 covers the distal end when attached so as to protect the light source 36, as well as any recharging connector, when in use. The end cap may be releasably attachable to the end of the main body 2 of the device so that a user can easily remove the end cap 38 to allow for recharging or battery replacement. In certain embodiments, at least a portion of the end cap 38 remains attached to the device, such as by a hinge, wire or tether looped or connected to the inside of the device, to allow servicing or cleaning of the device while the attached portion prevents inadvertent loss of the end cap. Generally, the end cap 38 is dimensioned so as to be fittingly received within the distal opening of the main body housing 20, and may attach to the main body 2 by any of an interference fit, snap fit, a mechanical coupling or other suitable means of attachment. In certain embodiments, the distal lens tip is non-removable and includes a central port which acts as both an air intake and a recharging port, as shown in the device of FIGS. 6A-6D for example.

IV. Power Source

In an example embodiment, the device includes a portable power source, such as one or more batteries. In certain embodiments, such as that shown in FIG. 2A, the power source 30 includes two lithium ion based rechargeable batteries placed in series, that are non-removable by a user and are recharged, such as through a distal connector cord or other suitable recharging means. In some embodiments, the power source 30 may include removable batteries that may be easily removed and replaced by a user as needed. In other embodiments, the device utilizes one or more ultra capacitors in place of or in addition to the batteries described above. Additionally, it is appreciated that the device may operate with a conventional power cord if desired.

Figure 14B:
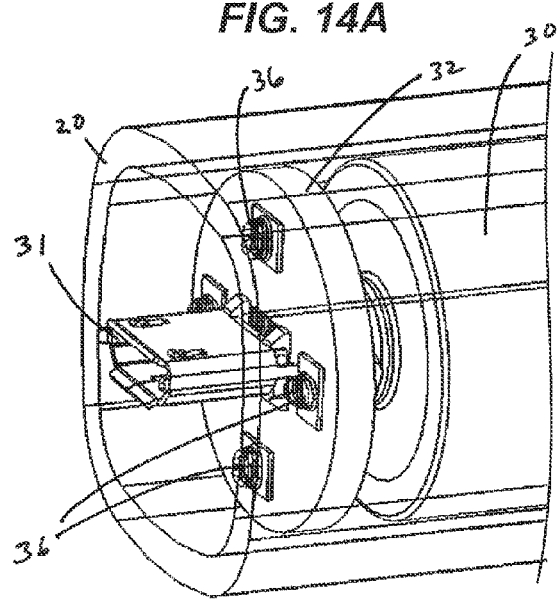
Figure 14C:
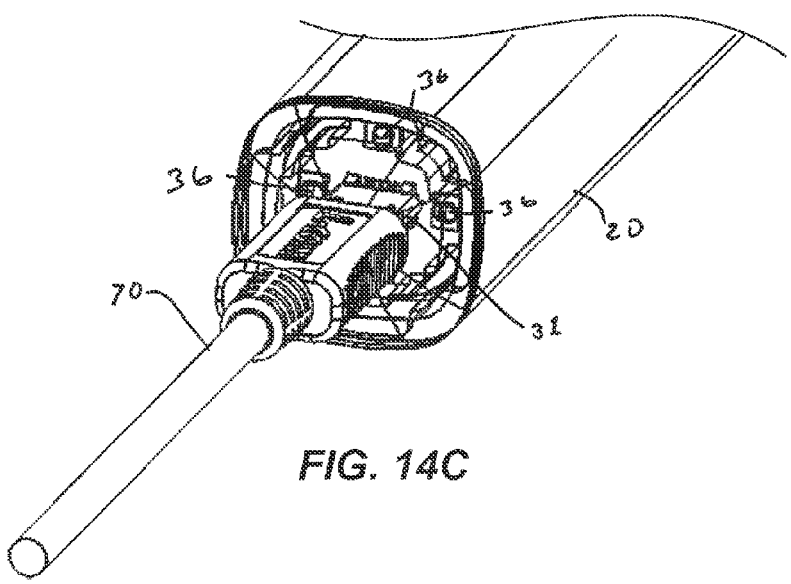

In certain embodiments, such as shown in FIGS. 14A-14C, the device includes a port 31 to recharge the power source 30, such as a micro-USB charging port located on a printed circuit board behind a distal lens tip or endcap. The port may be used to recharge non-removable batteries by connecting a recharging cable 70, such as a USB cable, to the port, which may utilize a wall charging adapter or cigarette lighter adapter in an automobile. In an example embodiment, the device includes two 3.7 V lithium ion batteries placed in series, which are charged by electrically coupling the batteries to an external wall supply with a current of about 1.5 A to 1.8 A. Generally, the maximum charging current drawn is 1.8 A and a completely discharged device may take from 1 to 2 hours to fully charge. As shown in FIGS. 14A-14C, the device may include a recharging port 31 for connecting with a USB cord 70 for recharging of the rechargeable power source 30, as described above.

In certain embodiments, such as shown in FIGS. 15A-15C, the device includes a bulb heater mounted on a lamp holder within a bulb chamber. The bulb may be any bulb suitable for sufficiently heating the substance to vaporize an active ingredient therein for inhalation by the user. In certain embodiments, the bulb heater comprises a halogen tungsten quartz bulb, which are particular useful when used in a vaporization device in accordance with the present invention since such bulbs have a high visible-near infrared output with little UV, a smooth spectrum and stable output. These characteristics allow for a consistent and reliable heat source that can be controlled to maintain a desired temperature level within a chamber in which the bulb is disposed. In certain embodiments, the bulb may be disposed in a separate chamber adjacent a cavity in which the substance is disposed and may be adapted to heat and vaporize the selected substance using one or more of radiative, convective and conductive heating. In an embodiment utilizing conductive heating in combination with radiative and convective heating, the bulb heater may protrude directly into the cavity or into the grinding cavity so that the glass bulb directly contacts the contents of the grinder.

For example, as shown in FIGS. 15A-15D, the distal portion of the device includes a PCB 23 electrically coupled with a lamp holder 57 on which the bulb heater 53 is mounted protruding proximally within the grinding chamber such that the glass of the bulb contacts the selected substance in the chamber sufficiently to vaporize an active ingredient in the substance. The PCB 23 is adapted to selectively energize the bulb heater 53 based on a temperature measurement from a thermistor 55 disposed adjacent the bulb to inhibit or prevent incineration of the selected substance during vaporization. The thermistor 55 may be mounted on the lamp holder 57 on which the bulb heater is mounted. The PCB 23 may be configured with one or more holes through which inhaled air passes so that the inhaled air passes directly by the bulb heater 53 providing efficient heating of the inhaled hair.

In any of the embodiments described herein, the device may include one or more screens to filter large particles from the inhalation screen and/or to cool the temperature of the inhalation stream before inhalation by a user. Since the screen or filters in the device may clog occasionally during use of the vaporizing device, the device may further include a cleaning tool 59 to allow a user to service or clean the device to ensure proper air flow and operation. In certain embodiments, the cleaning tool 59 may be removably attached to the device, either clipped onto the device within a groove or recess, such as shown in FIG. 15A, or may be configured to slide into a mouthpiece of the device and stowed internally within the device. In some embodiments, the cleaning tool has a pointed distal end to allow a user to clean or pick out residue adhered to the screen or various components of the device. In the example of FIG. 15A, the cleaning tool is a metal stamped tool that clamps over the housing of the device and fits neatly into a molded recession so as to lay substantially flush with an outer surface of the housing. A detail view of the cleaning tool 59 in the example of FIG. 15A is shown in FIG. 15E. In other embodiments, the cleaning tool may include a brush like tool or may be incorporated into the device itself.

Figure 16A:
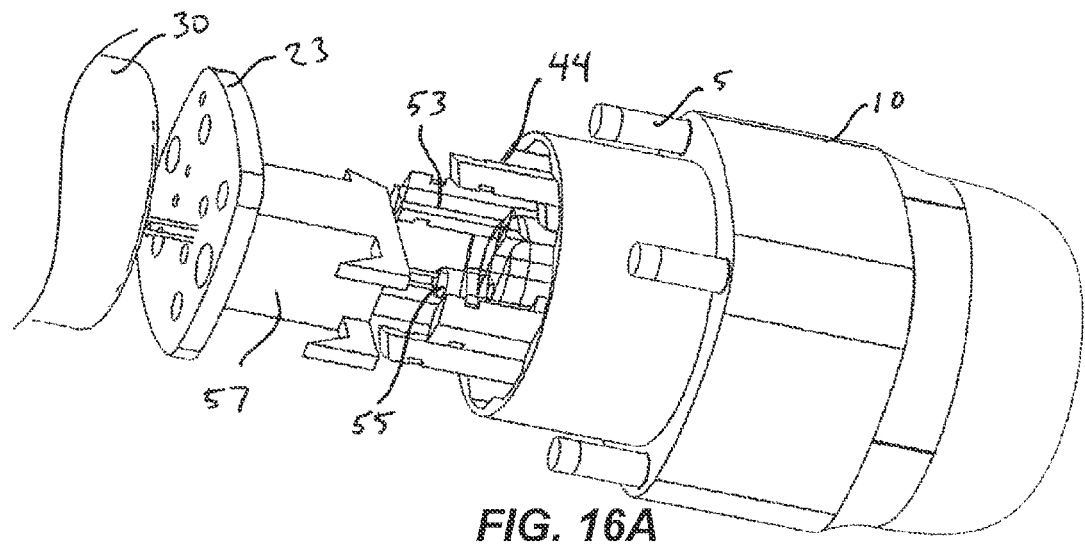
FIGS. 16A-16B illustrate detail views of the lamp holder, thermistor, bulb chamber and bulb heater of the example vaporizing device of FIG. 15A.
Figure 16B:
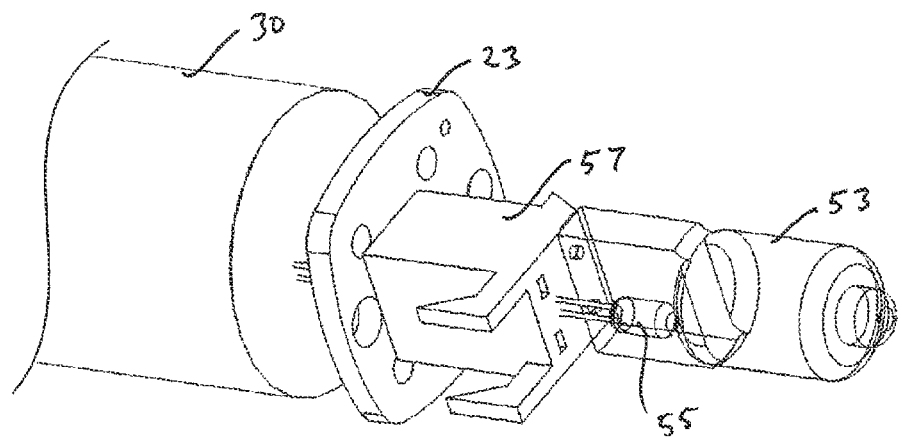

FIGS. 16A-16B depict detail views of an embodiment that utilizes a bulb heater, such as a halogen tungsten in quartz bulb, as a heating element. In this example, the heating chamber in which the bulb heater is disposed the grinding cavity itself, the bulb heater extending proximally into the proximal grinder 44 between the grinding teeth when mounted on the lamp holder 57 to contact the contents of the grinder, while a thermistor 55 is positioned at the base of the bulb heater 53 to allow controlled heating and vaporization as described herein. It is appreciated that in other embodiments, the bulb heater may be disposed in a separate heating chamber either separated from a grinding chamber or included in a device without a grinding chamber. FIG. 16B depicts the bulb heater 53 mounted to the lamp holder 57 prior to insertion within the cavity of proximal grinder 44 (the distal grinder 42 has been removed for viewing purposes).

In certain aspects, the power source 30 is configured, such as with a processor and/or micro-controller of the device, so as to activate the heating unit in response to detection of air flow through the device. In certain embodiments, detection of air flow is provided by a sensitive active thermistor or other sensor that can detect airflow in less than a second, generally within 0.5 seconds of inhalation, so that once airflow is detected, the heating unit is energized with the power source 30 so as to provide sufficient heat to vaporize the selected substance within less than 5 seconds, preferably within 2.5 seconds or less of being energized. A hot chamber thermistor disposed adjacent the heating unit, such as a thermistor disposed at the base of a bulb heater, may be used to control the power input from the power source to the heating unit so as to control the heating to maintain an air temperature within a chamber of the device at a temperature within a range of about 160° C. to 210° C., preferably 170° C. to 210° C., and even more preferably within 180° C. to 200° C. during vaporizing. In an example embodiment, the power source 30 is configured to maintain the desired temperature during inhalation, so as to conserve power consumption between inhalation or "puffs," thereby allowing for increased battery life. In some embodiments, the power source 30 may be configured to reduce power supplied to the heating unit in response to a detection of a temperature greater than a maximum temperature, such as 200° C. or if the coil has been continuously operating for more than 10 seconds. This aspect is useful as it may help prevent overheating of the device while increasing the useful life of a heating element 51, such as a heating coil, in a heating unit, such as shown in FIG. 3C. In some embodiments, the device includes a cutoff voltage, such as about 7.4 Volts, to maintain adequate battery life throughout the battery discharge range, so that a typical user can use the device for about 200 inhalations at the duty cycles described herein from a single charge. It is appreciated that any of these features described herein, particularly aspects relating to the power source and heating control, may be utilized in a vaporizing device using conduction to heat and vaporize the active ingredients of a selected substance. Such a device may utilize thermal conduction to heat the selected substance, such as by heating the grinding unit and/or a cavity containing the selected substance, to vaporize the active ingredient of the selected substance by conduction while providing increased control and consistency of vaporization, preserving the heating unit life and conserving power to extend battery life of the device.

In certain embodiments, the device includes one or more PCBs having a memory module with firmware recorded thereon that allows for controlled heating of the heating unit so as to provide sufficient heat to vaporize the selected substance without overheating. Generally, the device is configured so as to energize the heating unit with power sufficient to provide heating of air to at least 180° C., preferably about 188° C. In some embodiments, the device may include a switch allowing a user to select between one more temperature vaporization ranges, such as a low temperature range 100-150° C., a medium temperature range 150 to 175° C., and a high temperature range 175 to 200° C., the temperature range corresponding to the optimal vaporization temperature of the substance selected by the user or according to an individual user's preference. In some embodiments, the user may change the temperature by changing the duration or flow rate of an inhalation, for example using short puffs or light inhalations to vaporize a substance with a lower vaporization temperature and using longer puffs or stronger inhalations to vaporize a substance with a higher vaporization temperature. In other embodiments, the device may include a switch or mechanism by which the vaporization temperature is automatically selected upon insertion of a particular cartridge containing a pre-prepared substance, the automatically selected temperature range corresponding to the preferred vaporization temperature for the pre-prepared substance. For example, a cartridge containing a tobacco blend may be configured so that insertion of the cartridge selects the low temperature range, while a cartridge containing Ginseng is configured so that insertion automatically selects a high temperature range. In other embodiments, the variations in the cartridge design or the materials comprising the cartridge may be used to alter the vaporization temperature within the cartridge, for example a more thermally insulating cartridge may be used for a substance having a lower vaporization temperature, while a less insulating cartridge may be used for a substance having a higher vaporization temperature.

In certain aspects, the power required to provide suitable heating of air flow with the device may be determined using the following equations:

$$\Delta T = \frac{W}{\text{specific heat} \times \text{density} \times V} \quad (1)$$

wherein change in temperature is $\Delta T = °\text{C.} = \Delta K$;

wherein $W = \text{watts} = \frac{J}{s}$;

-continued $$\text{wherein volumetric flow} = V = \frac{L}{s};$$

$$\text{wherein Specific heat} = \frac{KJ}{kg \cdot K} = \frac{J}{g \cdot K}; \text{and}$$

$$\text{wherein density} = \frac{kg}{m^3} = \frac{kg}{kL} = \frac{g}{L}$$

Equation (1) may be used to calculate the power needed for a desired temperature of 188° C. (370° F.) using the following values. In this example, a temperature of 200° C. is used in the equations to account for heat/energy loss as follows:

$$\Delta T = 200°\,C. - 20°\,C. = 180°\,C. = 180\,K$$

The volumetric flow of air during typical inhalation through the device is estimated at:

$$V = 0.125 \frac{L}{s}$$

For airflow at 20° C. (room temperature)

$$\text{specific heat capacity of air} = 1.005 \frac{J}{g \cdot K}$$

$$\text{density of air} = 1.205 \frac{g}{L}$$

$$\text{specific heat} \times \text{density} = 1.21 \frac{J}{L \cdot K}$$

Using the above valued with Equation (1) yields:

$$180°\,K. = \frac{W}{1.21 \frac{J}{L \cdot K} \cdot 0.125 \frac{L}{s}}$$

$$W = \frac{J}{s} = \boxed{27.2 \text{ watts at } 20°\,C.}$$

wherein Watts (W) is Joules (J) per second (s);
For airflow at 200° C.

$$\text{specific heat capacity of air} = 1.026 \frac{J}{g \cdot K}$$

$$\text{density of air} = 0.746 \frac{g}{L}$$

$$\text{specific heat} \times \text{density} = 0.765 \frac{J}{L \cdot K}$$

$$180\,K = \frac{W}{0.765 \frac{J}{L \cdot K} \cdot 0.125 \frac{L}{s}}$$

$$W = \frac{J}{s} = 17.2 \text{ watts at } 200°\,C.$$

In the above equations, the power required to obtain heating of air to the target temperature of about 188° C. is about 27 Watts for air flow 0.125 L/s at 20° C. (room temperature) and 17.2 Watts for air flow of 0.125 L/s at 200° C.; thus, the power required upon initial inhalation is often higher than the power required once the heating unit has reached operating temperature. Therefore, many devices include a thermistor within the heating chamber or adjacent the heating unit so that the power supplied can be controlled and varied as needed to heat the air to the desired temperature. In certain embodiments, the device is configured to energize the heating unit with power of about 10 to 30 Watts, preferably about 15-25 Watts, even more preferably between 17 and 27 Watts. In some embodiments, the power supply is configured (such as with a microprocessor or microcontroller) so as to vary the power supply according to a characteristic of usage, such as temperature, air flow speed and/or elapsed time after inhalation is detected. For example, higher powers may be required to sufficiently heat the air flow for volumetric flow rates higher than 0.125 L/s, or if an initial temperature of air flow is substantially lower than room temperature. In certain aspects, the above factors are approximated and one or more duty cycles or predetermined power profiles may be used with each inhalation to provide sufficient power. For example, a typical duty cycle in terms of a ratio between heating time (e.g. the duration for which the heating unit is energized and heated) versus non-heating time (e.g. duration for which the heating unit is de-energized between heating times) may be within a range of about 10% to 50%, about 20% to 40%, or about 33%. In terms of duration, the duty cycle heating time versus non-heating time may be about 2-8 seconds "on" versus 5-15 seconds "off," about 3-6 seconds "on" versus 7-14 seconds "off," or about 5 seconds "on" versus 10 seconds "off." In some embodiments, the duty cycle may be set by a user, for example by changing the duration and frequency of inhalations during use. Some embodiments may further utilize the thermistor or an elapsed time to alter the cycle or power profile, for example to prevent the device from overheating or to limit the time which the heating element is continuously heated. Often, the device includes a cut-off time after which the heater will turn off when continuously heated, the cut-off time being a duration of about 10 seconds or less, 7 seconds or less, or, in some cases, 5 seconds or less, so as to allow for sufficient heating to vaporize the substance, while conserving power usage during use.

In an example embodiment, the device uses two batteries to provide the power required to energize the heating unit, as well as to activate and operate the LEDs, as described previously. In some embodiments, the device uses one or more ultra-capacitors to power the device. Use of an ultra-capacitor offers some advantages in that generally fewer ultra-capacitors are required than batteries of similar size, minimal if any battery management is needed, and ultra-capacitors can deliver higher powers than similar sized batteries, particularly when operating in strobe mode. FIG. 12 illustrates a circuit diagram utilizing ultra-capacitors, and the associated graph illustrates the voltages over time when operating the ultra-capacitors in a strobe mode having a 3-5 second strobe.

V. Control Electronics & Sensors

In an example embodiment, such as in FIGS. 5A-5B and FIGS. 6A-6B, the device includes various electronics and sensors for use in activating and controlling operation of the device, such as described above in regard to the power source 30 in the preceding section. The device includes printed circuit board components 32 having a memory module with firmware recorded thereon, for use in activating and/or controlling the heating unit and distal light source described above in response to various inputs from a user or various sensors or components of the device. In various embodiments, the device includes a thermistor (not shown) disposed adjacent the heating unit or within the airflow of the device for measuring temperature in real-time so as to allow dynamic adjustment of the heating unit temperature, and an inhalation sensor 34 for detecting air flow and velocity from user inhalation. The inhalation sensor 34 may be an air pressure sensor, such as capacitive type pressure sensor or a piezo resistive element, for example a MEMS gauge pressure sensor having low power consumption. In some embodiments, the device may use a combined temperature and pressure sensor such as a miniature digital barometer having both temperature and pressure outputs.

In an example embodiment, the outputs of the pressure sensor and/or thermistor are used to activate or control the heating unit and/or the distal light source, such as described above. Generally, when a user inhales, air velocity increases and the pressure sensor detects a sufficient pressure change sending an output signal to a PCB component, processor or microcontroller. In response to the signal, the heating unit is energized by the power source to provide sufficient heating; the power supply to the heating unit may be controlled or halted in response to an output from a thermistor or in response to various other variables, as described previously. In some embodiments, the heating unit temperature is adjusted in real-time with air velocity to maintain optimal vaporization, and the unit may be configured to turn itself off when inhalation ceases or after a specified time, such as 10 seconds or less. Air velocity data from the sensor can also be used as an input to the distal light source so as to allow for dynamic adjustment of the brightness of the LEDs at the distal tip of the device.

VI. Grinder

Figure 9A:
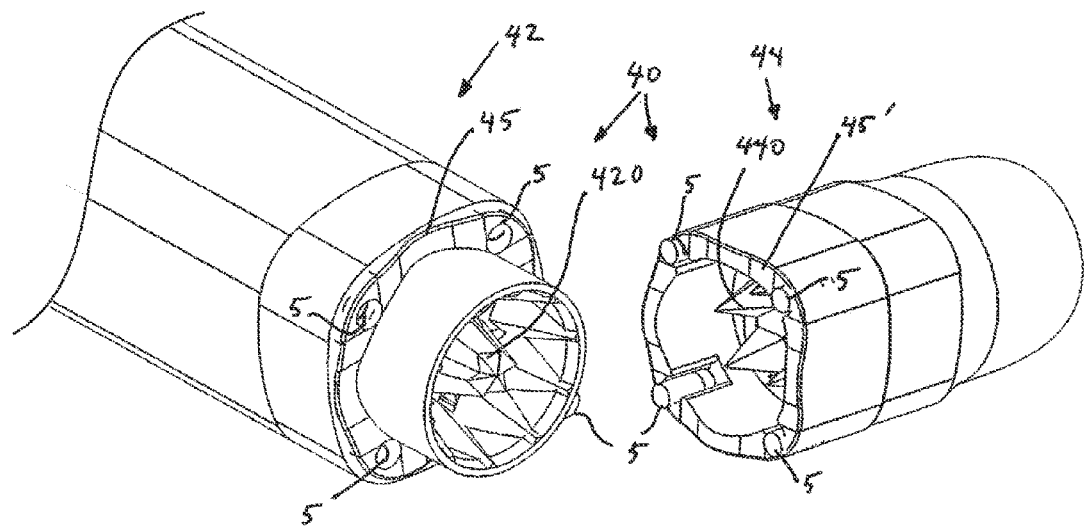
FIGS. 9A-9B illustrate components of an example grinder before and after assembly in a device.
Figure 9B:
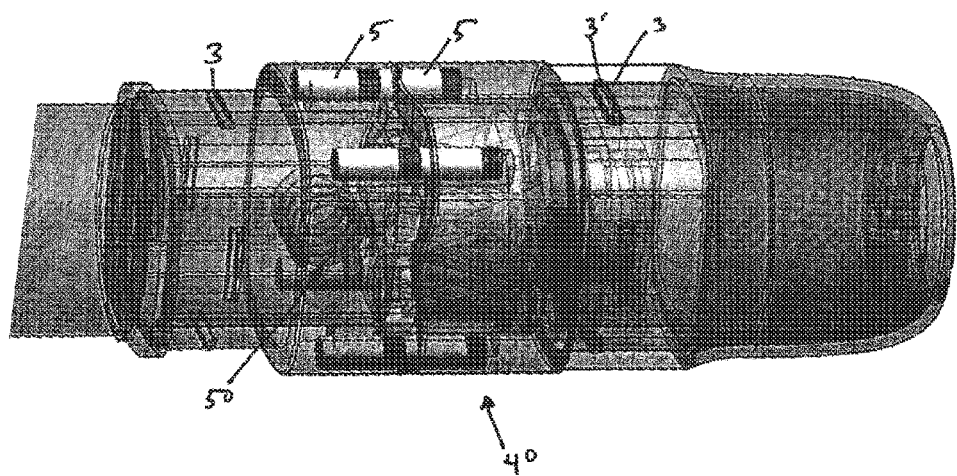

In certain embodiments, such as those shown in each of FIGS. 2A, 3C, 5A, 6A, 9A and 13, the device includes a grinder integral to the device for grinding selected substances having active ingredients therein, such as intact tobacco leaves or other herbal or plant matter, into minute particles suitable for vaporization of the selected substance for inhalation by a user. Generally, and as shown in the embodiment of FIGS. 9A-9B, the device includes a grinder 40 comprising a separable distal grinder portion 42 and proximal grinder portion 44, the distal portion 42 being disposed on a proximal end of the main body 2, and the proximal grinder portion 44 being disposed on the distal end of a proximal portion having a mouthpiece portion 1, although it is appreciated that the grinder portions could be included on various other components or may comprise detachable portions so that the grinder portion could be completely removed if desired. This configuration allows the user to detach the proximal grinder portion 44 from the distal grinder portion 42, place a solid substance into a cavity of the proximal grinder portion 44 (or alternatively in a cavity of the distal grinder portion 42), interface the two portions together (such as shown in FIG. 9B) and activate the grinder so as to grind the selected substance. The grinder 40 may be activated by manually rotating the distal grinder portion 42 relative to the proximal grinder portion 44, or vice versa. Although generally, the grinder is activated by applying rotational force through manual means, it is appreciated that the grinder may be activated in various other ways, such as through electronic means or by translating other forces, such as by translating axial force into a rotational force or vice versa.

A. Proximal Grinder Portion

In the above embodiment, the proximal grinder portion 44 of the grinder 40 slides over the distal grinder portion 42 and is visible as the "cigar band." The device includes one or more magnets distributed about interfacing surfaces of the proximal and distal grinder portions (often, one at each corner In certain embodiments having a cross-section shaped like a square with rounded corners). In certain embodiments, the grinder may also function as the vaporization chamber for the solid substance within. This may be achieved through holes in each of the proximal and distal grinder portions so as to allow air inhaled through the device to pass through the grinding cavity. These holes allow hot air to pass from the heater to vaporize the active ingredients within the ground substance and to flow out of the grinder carrying the vaporized active ingredients into the mouthpiece for inhalation. Examples of these holes can be seen in FIGS. 10A-10B, although in certain embodiments the holes may be considerably smaller or may include screens or filters proximal and/or distal of the grinder so as to prevent the contents of the grinder from traveling into the heating unit or mouthpiece.

In an example embodiment, one or both of the interfacing surfaces of the proximal and distal grinder portions are molded with a wave-guide orientation or undulating surface, as shown in FIGS. 9A-9B for example, so that with each twist, the proximal and distal grinder portions separate from each other during rotation and then reconnect as the magnets realign. This feature provides axial movement of the grinder portions relative to each other in addition to the rotational movement between grinder portions so as to create a mashing motion to facilitate breaking down of the selected substance. In some embodiments, this motion may also be used to help push the contents of the grinder into a separate vaporization chamber proximal and/or distal of the grinder chamber, although in certain embodiments the grinder chamber is also used as the vaporization chamber.

B. Distal Grinder Portion

In the above described embodiment, the distal grinder portion 42 rests against the housing surrounding the heating unit and is partially seated within the main body 2 to secure it in place. The interior chamber of the distal grinder portion 42 includes a protruding cylindrical member around which the proximal grinder portion 44 rotates. The distal grinder portion 42 includes a central burr 420 and grinding teeth 422 designed to fit into corresponding teeth 440 on the proximal grinder portion 44 so as to mash and grind the selected substance placed between the proximal and distal grinder portions as the components are rotated. Each of the magnets 5 (at each of the four corners) in the distal grinder portion 42 are positioned so as to align with corresponding magnets 5 disposed within the interfacing surface of the proximal grinder portion 44. In certain embodiments, the distal grinder portion 42 may be removable from the main body to facilitate cleaning.

In certain embodiments, the magnets 5 are used at interfacing portions of the distal grinding portion 42 and the proximal grinding portion 44, as shown in FIGS. 9A-9B, where the grinder portions come together. In this embodiment, there are four magnets 5 situated at each corner of each of the proximal and distal grinder portions. The magnets 5 help hold the two grinder pieces together to prevent contents from spilling (although the two grinder pieces may stay together under sheering force because the top piece slides over the bottom piece in a male/female connection) and provide a tactile response to users as they twist the proximal grinder portion so that users can more easily determine when the portions are aligned. Because the outer cross section of the grinder is a rounded square, as in the main body 2, the 4 corners align at 90 degree rotations. The interior cross section of the grinding chamber is substantially circular, so that the distal grinding portion 42 can rotate within the proximal grinding portion 44. It is understood that in some embodiments, the proximal grinding portion 44 can rotate within the distal grinding portion 42.

In many cases, this configuration may allow the outer cross section to rest at an odd angle, with the corners unaligned. Since this position may be considered undesirable for various aesthetic and design purposes, such a configuration is inhibited by the magnets, as their presence compels the user to complete the grinding rotation at 90 degree increments until the magnets are aligned.

VII. Mouthpiece & Cartridge

In an example embodiment, the device includes a mouthpiece portion to be placed within a user's mouth. This piece is contoured for user comfort, and in some embodiments, includes a rubber over-mold so users can bite down on the overmold to hold the unit comfortably in the user's mouth, typically hands free. The mouthpiece portion may be incorporated into the proximal portion, as shown in FIG. 2A, or may be removable from the proximal portion, such as shown in FIG. 3B so as to allow the user to replace the mouthpiece portion as the mouthpiece becomes worn over time, or between users. The mouthpiece portion may also include a cavity for holding the capsule 60, as shown in FIG. 2A. In this embodiment, the capsule or cartridge 60 sits in the mouthpiece directly in the hot air path from the heater and allows the heated air to pass through and/or around the cartridge, vaporizing the active ingredients of the selected substance disposed within. The selected substance in the cartridge may be in various forms, including a liquid or gel solution of propylene glycol/vegetable glycerin/nicotine, a powder, wax, oil, or a solid brick of the selected substance. In certain embodiments, the capsule or cartridge may contain flavors or colorings in lieu of or addition to actively vaporized substances. It is understood that the mouthpiece may instead or additionally be imbued with flavor. In certain embodiments, the capsule can be placed directly within the grinding cavity, such as in the device of FIGS. 6A-6D.

VIII. Screens/Filters

In an example embodiment, the device includes various filters, screens and membranes positioned at one or more locations within the air pathway extending through the device. For example, the main body 2 may include one or more filters or mesh screens to prevent dust or other particles from being drawn into the heating unit 50. In certain aspects, the device includes a small finely woven metal screen that sits over the holes at the entrance to the distal portion of the grinder. This small screen prevents ground debris from falling out of the grinding chamber into the main body or the heating unit. The small screen may be secured in a removable housing so that it can be easily removed for quick cleaning and/or replacement. The device may include the screen proximal and/or distal of the grinder portion so as to prevent minute particles from the grinder from traveling into the heating unit or through the mouthpiece. In another aspect, the device includes screens of varying sizes, for example a relatively large screen may be used distal of the grinder, while a screen having a finely woven metal mesh may be used at the exit of the proximal grinder portion. This larger screen prevents ground debris from falling out of the grinding chamber into the heating unit, and the fine screen helps limit the particle size in the vapor passing into the mouthpiece for inhalation. The screens may also be secured in a removable housing so as to be easily removable for quick cleaning and/or replacement. The mouthpiece portion 1 may also include one or more filters or membranes to filter the vaporized particles or to help control the air flow rate through the device.

A vaporizing device in accordance with the present invention, including any of the aspects described above, can be further understood by referring to the drawings and descriptions thereof, as follows:

FIGS. 1A-1B show perspective views of an example electronic vaporizing device 100 in accordance with the present invention. The device 100 includes a proximal portion having a mouthpiece 1 from which a user inhales the vaporized substance using the device 100 and a main body 2 housing the power source and electronics of the device 100, including the heating source for vaporizing the selected substance and a light-emitting assembly or LED disposed near the distal end covered by a translucent or clear end-cap 38. In the embodiment shown, main body 2 is releasably coupled with the grinder portion 40, and can be detached to load the selected substance into the device and/or to exchange batteries or the like. The mouthpiece portion 1 may also be releasably coupled to the grinder portion 40, such as with coupling mechanism 3, 3' as shown in FIG. 3C. It is appreciated that the main body 2 may be coupled with the grinder 40 and/or the mouthpiece 1, or any number of detachable or releasable components coupled by any suitable means. The main body housing 20 of the main body 2 and the housing 10 of the proximal portion of the device may be fabricated from the same or different materials. The outer shells of each portion have generally similar shape, or a shape that varies along the length of the main body 2, the proximal portion and/or mouthpiece portion 1. For example, as shown in FIG. 1A, the distal portion of the mouthpiece portion that interfaces with the grinder 40 (or main body 2) may have a square cross-section with rounded corners to facilitate a smooth transition, while the proximal portion of the mouthpiece portion may have a substantially circular cross-section to facilitate placement in a user's mouth.

In certain embodiments, the distal portion 2 houses the power source, often two cylindrical batteries placed in series, as well as a heating source, a distal light emitting diode and associated electronics, including one or more PCB circuit boards. The outer shells may be constructed in a variety of shapes, although in various embodiments described herein, the mouthpiece portion has a substantially cylindrical shape and the outer shell 20 of the main body 2 has a substantially square cross-section having rounded corners, such as shown in FIGS. 1A-1B. The more circular cross-section of the proximal mouthpiece portion facilitates insertion of the proximal portion into a user's mouth for inhalation of the selected substance, while the substantially square shape of the outer shell 20 forms four air-flow channels 6 (one at each corner) when cylindrical batteries are placed within.

FIGS. 2A-2B illustrate a cross-sectional view of the example vaporizing device in FIGS. 1A-1B along section lines A-A and B-B shown in FIG. 1B. In FIG. 2A, the internal components described above can be seen in greater detail disposed within the outer housing 10 and 20 of the device. The proximal portion 1 includes a proximal end, a distal end and a passageway extending therethrough. At the proximal end is an inhalation opening 4 to be placed in a user's mouth to allow inhalation through the device. The proximal portion may further include additional components within the passageway, such as screens, filters, and thin films (not shown) that may reduce the quantity of contaminants and/or larger particles inhaled during vaporizing with the device. The distal portion includes a distal grinder portion 42 which interfaces with the proximal grinder portion 44 of the distal portion 2 when the components are assembled during use so as to form a grinder 40. Rotating the proximal portion 1 relative the distal portion 2 moves the corresponding burrs of the grinder 40 so as to grind and eviscerate the selected substance placed within the grinder. The proximal portion 1 may also include a capsule or cartridge 60 in which various pre-prepared substances, including various liquids, gels, waxes, oils, powders, solids or mixtures thereof, may be placed so that heated air drawn through the device passed through and/or around the capsule so as to heat and/or vaporize the active ingredients within the selected substance for inhalation. The capsule 60 may be located at any point within the passageway between the heater and the inhalation opening, such as in a central portion as shown in FIG. 2A, or in some embodiments, placed directly within the cavity of grinder.

As shown in FIG. 2A, the distal portion 2 of the example embodiment includes a proximal end, a distal end, and a passageway extending therethrough. The proximal end of the main body portion 2 includes the proximal grinder portion 44, and the distal end includes the distal end cap 38 covering a distal light source 36 and an optional recharging connector or port (not shown). The power source 30, light source 36, heater 50 and associated electronics are disposed within the passageway extending therebetween. In certain embodiments, the heater includes a heating screen or coil disposed adjacent the grinder and/or capsule cavity, while the power source includes one or more batteries disposed within the central portion of distal portion 2. As can be seen in FIG. 2B, the slightly square cross-sectional shape of the distal portion 2 creates four passageways 6 around the battery which allow the air drawn into the device to be drawn from the distal end of the device so as to more closely simulate the sensation of drawing air through a real cigarette or cigar. Additionally, this feature allows the air intakes to be located away from the central portion of the device which prevents the air intakes from being covered by a user's fingers when the device is held during use. This aspect also allows air drawn in to cool the electronics and power source so as to prevent overheating of the device during use, which may further increase efficiency by transferring heat to withdrawn air even before the air is passed through the heater. In certain embodiments, the power source 30 includes one or more lithium based rechargeable batteries, placed in series that are non-removable and are rechargeable through a distal connector cord or other suitable recharging means. In some embodiments, the power source 30 may include removable batteries that may be removed and replaced as needed. In other embodiments, the device utilizes one or more ultra capacitors in place of or in addition to the batteries described above.

In the embodiment shown in FIG. 2A, the distal portion includes a distal light source 36 covered by a translucent or clear end cap 38. The portion of the end cap 38 that interfaces with the distal end of the distal portion 2 may include gaps or openings 8 to allow airflow into the passageway extending through the distal portion 2 upon inhalation by a use, or alternatively a central air intake port, such as in FIGS. 6A-6D for example. In certain embodiments, the distal end also includes a recharging port 31, such as in a USB connector 31 or a pin receptacle as shown in FIGS. 6A-6D, so as to facilitate recharging of the power source therein. The distal end cap 38 covers the distal end when attached so as to protect the light source 36, as well as any recharging connector 31, when in use. In some embodiments, the end cap 38 is releasably attachable to the end of the distal portion 2 so that a user can easily remove the end cap 38 to allow for recharging or battery replacement.

An example device includes various electronic components including the heating unit 50, a distal light source 36, as well as a thermistor (not shown) disposed near the heater 50 for sensing temperature within the device, and a pressure sensor (not shown) for detecting inhalation or air flow through the device. The air flow sensor (not shown) may be disposed in any location within the device suitable for measurement of air flow. The output of the air flow sensor is also used in activation of the distal light source 36, as described above. The electronics configured to control the above components may be disposed on one or more printed circuit boards (PCBs), and may include a memory module containing firmware that controls operation of the device, the PCBs often being disposed adjacent the power source.

The air flow sensor (not shown) may be disposed in any location within the device suitable for measurement of air flow. The output of the air flow sensor may be used to initiate heating and to activate the distal light source 36, as described above.

In the embodiment shown in FIGS. 3A-3B, the device includes a main body housing 20 having a cigar like shape, having a square shaped cross-section with rounded corners. The device includes a detachable mouthpiece portion 1 near the proximal end and a grinder portion resembling a "cigar band" distal of the mouthpiece portion 1. As can be seen in FIG. 3B, the housing 10 of the grinder portion 42 may include protruding coupling features 3 on each side of the outward facing surface that are resiliently received within a corresponding coupling recess 3' on an inside surface of the housing 20 so as to releasably couple the distal grinder portion 42 to the main body 2.

In certain embodiments, the device includes a heating unit 50 comprising a heating element coil 51 that heats to the desired temperature in response to an activation mechanism. The activation mechanism may be a switch combined with an inhalation sensor so that the switch energizes the heating unit 50 in response to a detection of inhalation by the sensor. The switch mechanisms may include one or more of a tilt sensor, a heat sensor on the mouthpiece for sensing when the device is placed within a user's mouth, a pressure sensor for detecting when the device is held by the user, or a sensor that detects mouth suction as the user begins inhaling through the device. An inhalation sensor may be particularly useful in some embodiments as it avoids many of the drawbacks associated with tilt sensors, heat sensors and pressure sensors, which include accidental activation. To reduce wasted power consumption associated with dark current (e.g. current drawn by one or more sensors when the device is not being used), the activation mechanism may comprise a "ball switch" that energizes the heating unit in response to inhalation by a user, described in more detail in FIGS. 4A-4B.

In certain embodiments, the proximal portion is detachable using the rectangular coupling features 3, 3' as described above. Similarly, the detachable mouthpiece portion includes protruding portions 3 on each side that are resiliently received with four corresponding rectangular recesses 3' on an inside surface of the housing 10 of the proximal grinder portion 44, thereby enabling a user to easily detach or attach differing mouthpieces as needed.

In an example device having multiple detachable components, such as shown in the embodiment shown in FIGS. 3A-3B, the device 200 allows for insertion of a selected substance into the grinder cavity and insertion of a cartridge having a pre-prepared substance disposed within. The main body 2 of device 200 includes a lens tip 38 at its distal tip and an inhalation sensor 34 at its proximal end. The proximal end further includes a coupling means at its proximal end for releasably coupling with the heating unit 50 and the distal grinder portion 42 of the grinder 40, which in turn releasably couples with the proximal grinder portion 44, which in turn couples with the mouthpiece portion 1, often with similar coupling means. In the embodiment shown in FIGS. 3A-3D, the coupling means includes four rectangular protrusions extending radially outward along each side of the distal grinder portion 42 which are resiliently received within corresponding rectangular recesses within an inside surface of the main body 2, such as shown in detail in FIG. 3C, so as to releasably couple the components, although it is appreciated that the releasable components can be coupled with any suitable attachment means. These releasable coupling features may be used to clean and/or replace various components, such as the distal grinder 42 or the heating unit 50. In certain embodiments, such as that shown in FIG. 3B, the distal grinder 42 and proximal grinder portion 44 components are releasably coupled by a dimensional fit which is assisted by the presence of four permanent magnets 5 on each corner of the proximal grinder portion 44 that align with four corresponding permanent magnets 5 on the distal grinder portion, as discussed above.

In the embodiment shown in FIGS. 3A-3D, the heating unit comprises a heating element 50 and a cone-shaped reflector 52. The heating element 50 is a coiled wire, and may be fabricated from Nickel Chromium, positioned within the air flow through the device 200 so as to transfer heat by convection to the air flowing therethrough during inhalation by the user. The coiled wire or filament may be designed so as to support itself within the proper position, or may be attached to one or more metal or other meshes or frameworks. As shown, the heating element 50 is positioned along an axis transverse to a longitudinal axis of the device 200 so as to more efficiently transfer heat to the flow of air directed substantially perpendicular to the axis about which the wire coils; although, a variety of different configurations and alignments of the heating element 50 are within the scope of the invention. The heating unit further comprises a reflector 52, which is generally a cone shaped polished surface that reflects the radiative heat emitted by the heated coil; thus, the heating unit shown provides increased efficiency in heating by utilizing both convection and radiation to heat the air sufficiently to vaporize the selected substance proximal of the heating unit. The device 200 may further include a thermistor (not shown) disposed adjacent the heating unit so as to allow for more control over heating of the selected substance. Temperature readings from the thermistor may be used in a temperature feedback mechanism, or the heating unit may be configured to operate within a pre-determined range of temperatures suitable for vaporizing the active ingredients of one or more selected substances for inhalation.

As shown in FIG. 3C, the distal grinder portion 42 is located just proximal of the heating unit 50 so that air flow through the assembled device flows from the heating unit through a grinding cavity between the distal grinder portion 42 and the proximal grinder portion 44, so as to heat and vaporize the contents of the grinder for inhalation. As shown in FIG. 3D, the device may further include a funnel 56 that fits within the distal opening of the mouthpiece 1. The funnel 56 may be shaped to direct air flow through the mouthpiece, and may further include a receptacle for receiving a cartridge or capsule which may contain a pre-prepared vaporizing substance. As configured in FIG. 3C, the mouthpiece portion 1 of device 200 may be removed to insert a capsule for vaporizing, or alternatively, the proximal grinder portion 44 may be removed and a selected substance inserted for grinding and vaporizing with the device. Alternatively, the cartridge or capsule may be placed directly within the grinding cavity.

In an example embodiment, the device includes an inhalation sensor and/or switch for detecting inhalation. The inhalation sensor may comprise one or more airflow sensors positioned at any suitable location along the air flow so as to detect air flow through the device when a user inhales through the mouthpiece. The inhalation sensor may be used in controlling or adjusting the heating unit, activating the LED unit at the distal end of the device, or in turning on the device and activating the heating unit. By activating the device when inhalation is detected, this configuration conserves energy from the power source and allows the device to be used for longer periods of time before recharging. In an alternative embodiment, the device may include a combined switch/inhalation sensor, such as the ball type switch shown in FIG. 3B.

Figure 4A:
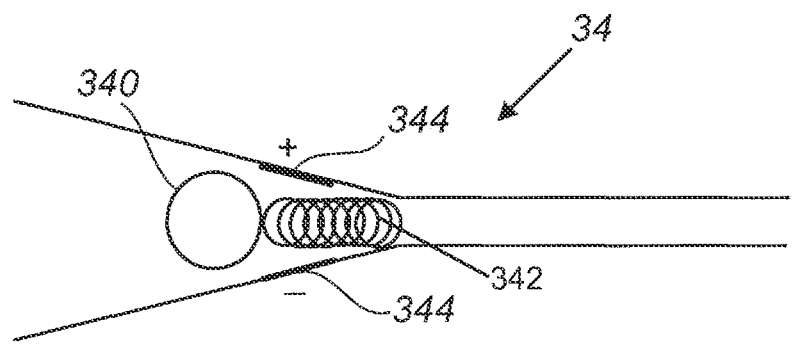
FIGS. 4A-4B illustrate an example activation switch having a ball and spring for use in a device.
Figure 4B:
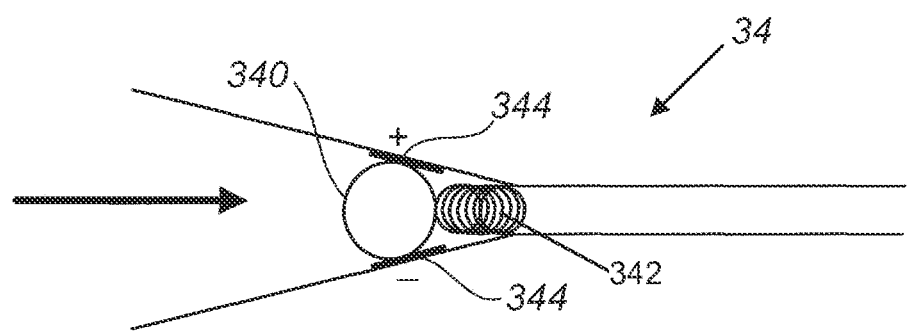

FIGS. 4A-4B illustrate the combined inhalation sensor/activation switch shown in the embodiment of FIG. 3A-3D. The sensor/switch 34 may include a conductive sphere 340, such as a plastic sphere with a metallic coating, such as silver that when sucked against the spring 342 by the force of inhalation, the sphere touches electrical contacts 344 which completes a circuit and activates the device, which in turn heats the heating unit to facilitate vaporization and inhalation of active ingredients of a selected substance with the device in a few seconds or less. Once inhalation ceases, the force of the spring 342 pushes the conductive sphere outward and the circuit is broken, thereby turning off the heater when not in use. This configuration prevents current usage when the device is not in use, thereby conserving energy and prolonging the time between recharging of the power source.

In the embodiment of FIG. 5A-5B, the device 300 includes a plurality of printed circuit boards PCB that are stacked within the device. The PCBs are round in shape so as to allow airflow around the PCBs when stacked within main body 2, which has a generally square shaped cross-section with rounded corners. In other embodiments, such as in FIG. 15A-15D, the PCBs are similar in shape to the main housing cross section, and create a pressure cavity by which a pressure sensor measures air flow. Although the PCBs Although the PCBs are shown disposed in the distal most portion of the main body, it is appreciated that the PCBs may be incorporated into various areas of the device. The PCBs often include firmware or programmable instructions recorded thereon for effecting controlled heating with the heating unit, such as in response to outputs from an inhalation and/or temperature sensor or for use in activation of the LEDs under lens tip 38.

In the embodiment shown in FIG. 6A-6D, device 400 includes elongate PCBs 32 that are positioned substantially parallel to the longitudinal axis through the device 400. The device 400 further includes an inhalation sensor 34 disposed between the PCBs. This configuration of the PCBs facilitates airflow through the distal portion of the device and more rapid detection of inhalation with the inhalation sensor 34, such as by detection of a change in air pressure, in this case a decrease in pressure. This further reduces the lag time between inhalation and heating of the heating unit to the desired vaporization temperature, thereby allowing a user to inhale the vaporized substance by inhaling directly through the device. The embodiment shown in FIG. 6A-6D includes an alternative lens tip from that depicted in FIG. 2B, the distal lens tip having a central conduit which doubles as a distal air intake passageway 8 and a distal charging port, such as for insertion of a small cylindrical connector pin for recharging of the power source.

Figure 7:
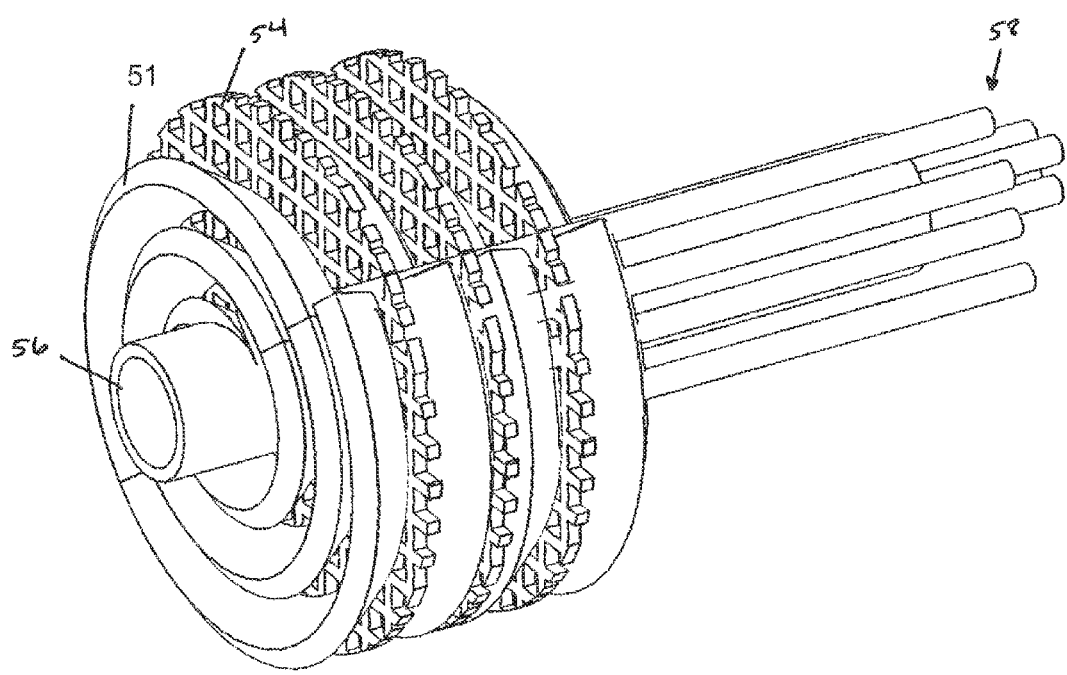
FIG. 7 illustrates an example heating unit for use in a vaporizing device.
Figure 8B:
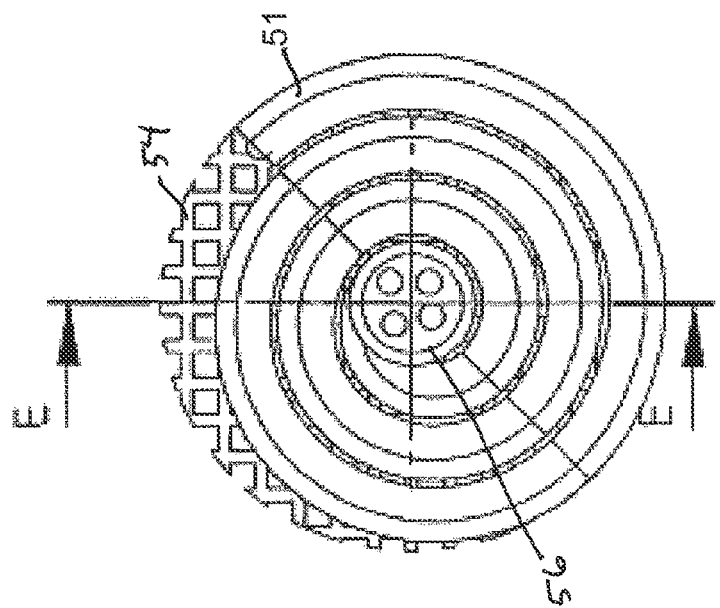
FIGS. 8A-8D illustrate various views of the example heating unit of FIG. 7.
Figure 8A:
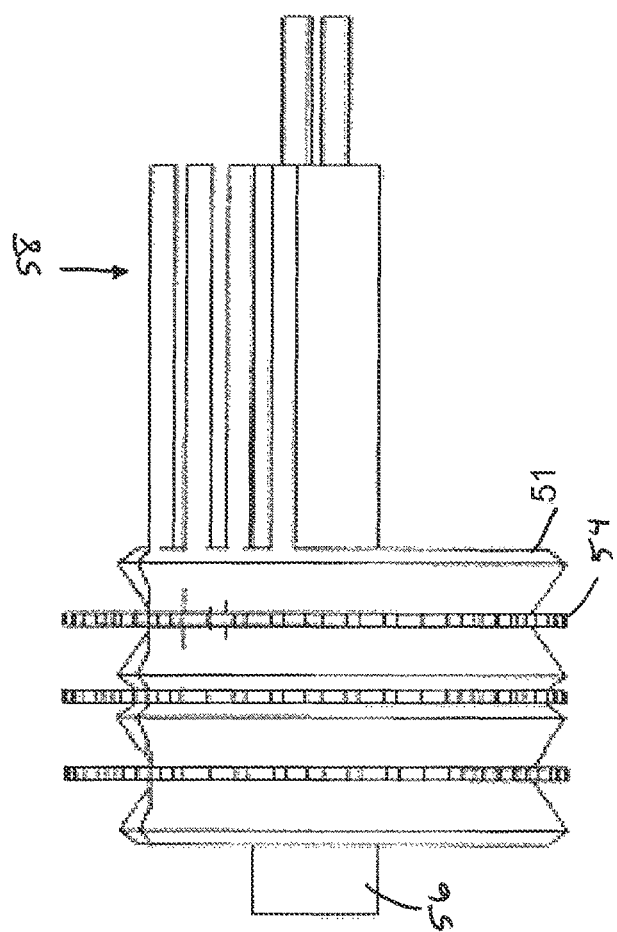
Figure 8C:
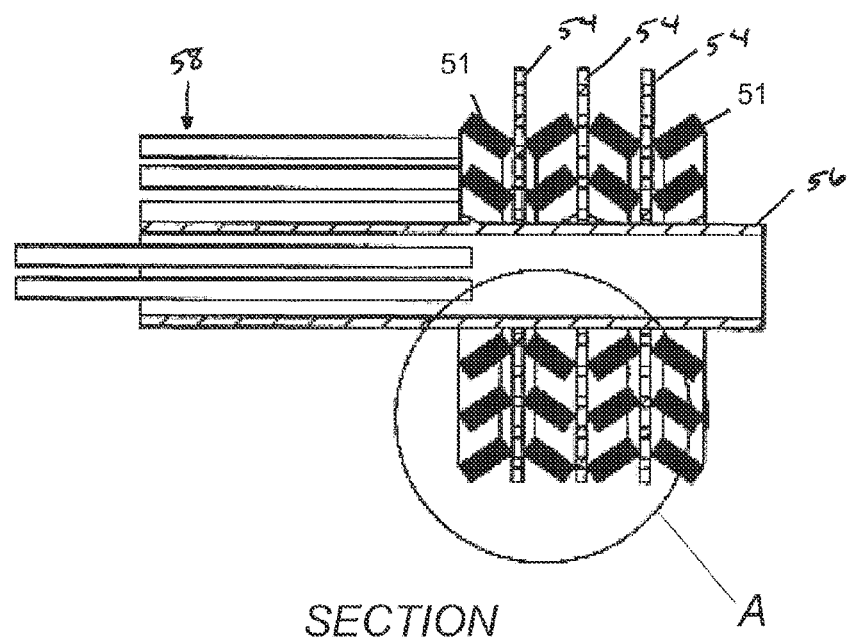
Figure 8D:
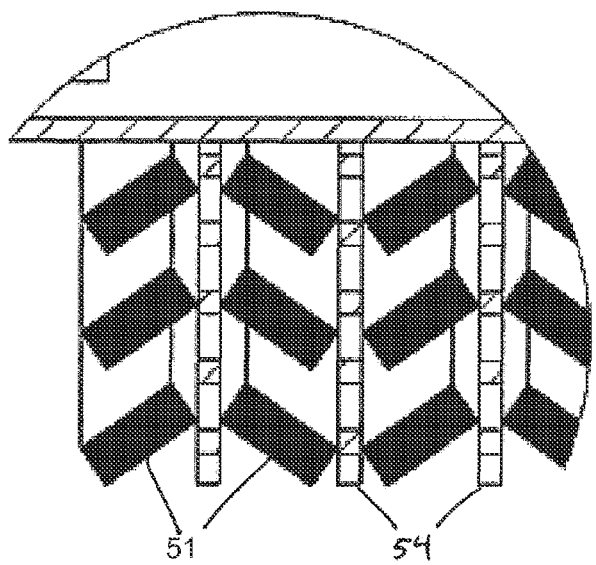

FIG. 7 illustrates an alternative heating unit 50, which includes four heating elements 51 shapes as coils separated by a wire mesh 54. Each heating coil has a positive and negative terminal and leads 58 extending distally from the coil to the power source. As shown, the leads 58 extending from one terminal of the coil may extend distally, while the leads 58 extending from the opposite terminal may extend distally through a central cylinder 56, so as to protect the leads from the elevated temperatures at the center of the heating unit 50 and prevent overheating as well as shorting of the leads. FIGS. 8A-8D illustrate various side views, cross-sections and details of the heating unit 50 in FIG. 7. FIGS. 8C-8D illustrate angling created by the position of each heating coil relative to the other coils to create turbulent flow as air passes through the heater, thereby distributing heat through the flowing air more efficiently than during laminar flow.

FIGS. 9A-9B illustrate the interfacing components of the internal grinder 40 of a device in accordance with many embodiments of the invention. As can be seen in FIG. 9A, the distal grinder portion 42 includes a cylindrical portion that is dimensioned so as to be fittingly received within the cylindrical receptacle of the proximal grinder portion 44. The interface between the protruding cylinder of distal grinder 42 and the cylindrical receptacle of the proximal grinder portion 44 allows the components to be rotated relative to one another, the burs on the interior grinder surfaces rotating relative to one another so as to grind and break down any solid substance disposed within. The distal and proximal grinder portions include one or more holes so as to allow passage of heated air therethrough after grinding of the selected substance placed within. The outer edges of the distal grinder portion includes an undulating surface 45 that interfaces with a similar corresponding undulating surface 45' in the proximal grinder portion. The undulating surface 45 of the distal grinder portion 42 engages the undulating surface 45' of the proximal grinding portion 44 while the proximal grinder portion 44 is rotated relative to the distal grinder portion 42 causing an alternating axial movement of the components relative to each other so as to mash or further grind the selected substance with a slight axial movement as well as the rotational movement of the burrs of the grinder. For example, when rotating the proximal grinder portion 44 relative to the distal grinder portion 42, the peak of the undulating surface 45 engages a peak of the undulating surface 45' so as to slightly axially separate the distal and proximal grinder portions, and continuing rotation or twisting of the grinder portions cause the peak of the undulating surface 45 to rotate into a valley of the corresponding undulating surface 45' allowing the grinder portions to come together, as shown in FIG. 9. Although undulating surfaces 45 and 45' are shown on each of the grinder portions, it is appreciated that the undulating surface could include a variety of differing surfaces and protrusions to provide a similar effect. As described previously, the magnets 5 disposed at each corner of the grinder components facilitate alignment of the components in a more desirable, aesthetically appealing configuration.

FIGS. 10A-10B illustrate a distal grinder portion 42 and a proximal grinder portion 44 of an example grinder in accordance with certain embodiments. As can be seen in FIG. 10A, the distal grinder portion includes a protruding cylindrical housing surrounding a grinding cavity having a plurality of burrs or sharp angled surfaces. The grinding surface may include a plurality of grinding teeth 422 distributed about the circumference of the interior wall of the cylindrical housing and a central burr or masher 420, the grinding teeth interfacing with corresponding burrs (not shown) disposed within a cylindrical receptacle of the proximal grinder portion 44 in FIG. 10B. Optionally, the proximal grinder portion 44 may include a central hole 443 that interfaces with the central masher 420, which in some embodiments, may allow the contents of the grinder to be pushed through by the mashing or axial movement of components 42 and 44 relative to each other during grinding by rotating the components as described above. The proximal grinder portion 44 may further include additional holes 442 to allow the grinding contents to empty into a proximal cavity, or to allow air flow through the cavity of the grinder. The burrs and grinder may be configured so that the grinding action "pushes" the selected substance during grinding through one or more holes in the proximal or distal grinder portion into a separate cavity for vaporization. It is understood that in some embodiments, the coupling of the distal grinder portion 42 and the proximal grinder portion 44 may be reversed in such a way that the cylindrical housing protrudes from the proximal grinder portion and the cylindrical receptacle sits within the distal grinder portion, with the corresponding grinding teeth and burrs and masher reversed as well.

Figure 11A:
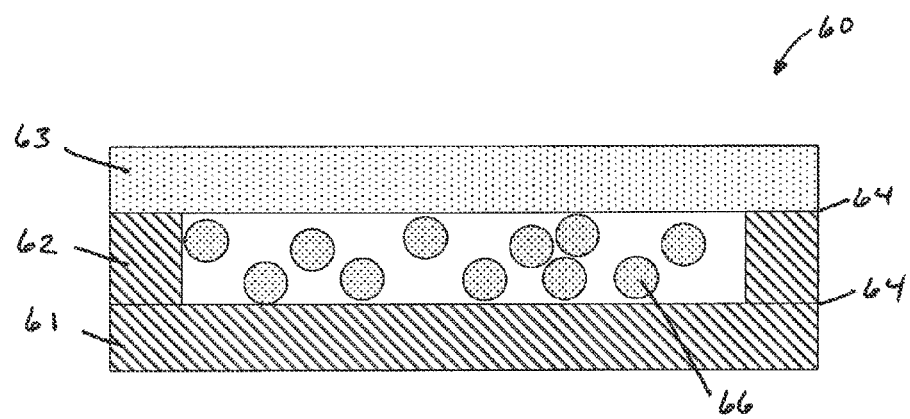
FIGS. 11A-11B illustrate an example cartridge or capsule for use in a device.
Figure 11B:
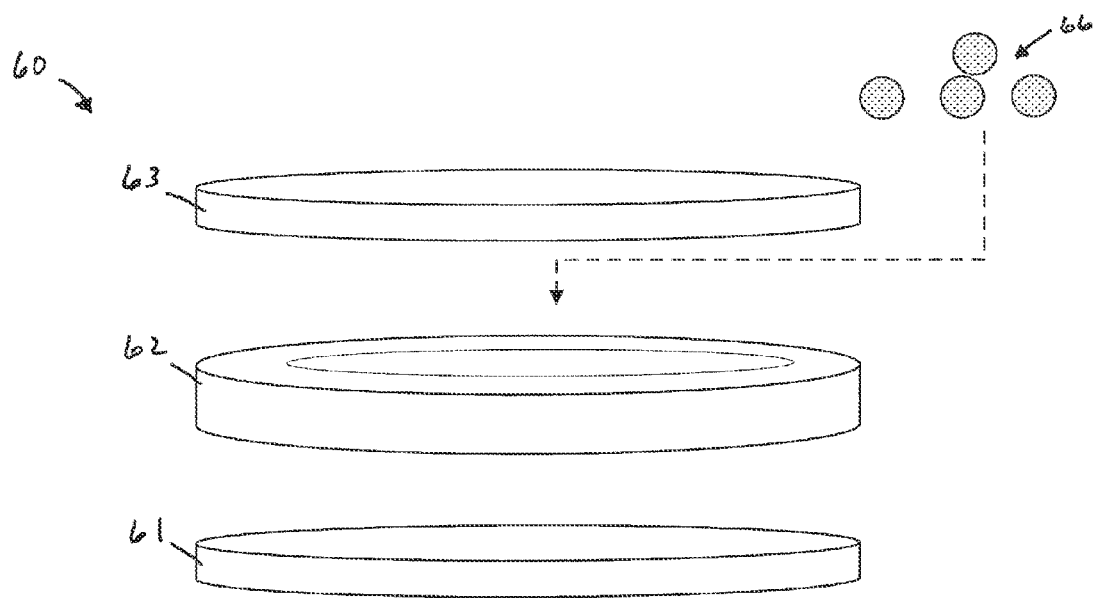

FIGS. 11A-11B illustrate an example cartridge or cavity for use with an electronic vaporizing device. Typically, the cartridge is supplied by a manufacturer and is pre-loaded with any of a variety of pre-prepared vaporizing substances, including but not limited to a liquid or gel solution, such as a propylene glycol mixture, a powdered or pre-ground substance, a wax or oil, or a solid brick of material suitable for vaporizing. The cartridge may further include additional heat conducting features to facilitate more uniform heating and vaporization of the material disposed within, such as conductive meshes, screens, or heat retaining features that extend through the material disposed within so as to conduct heat throughout the interior of the cartridge. Optionally, the cartridge may be configured to allow a user to load the cartridge with the selected substance of the user's choice.

As shown in FIG. 11B, the cartridge may comprise three layers, a bottom layer 61, a ring 62 in which a selected pre-prepared substance 66 is placed and a porous layer 63 on top. The layers may be fabricated from materials, for example a polytetrafluroethylene such as Teflon®, that can withstand the elevated temperatures needed for vaporization of the selected substance contained within the cartridge. After assembling the layers with the selected substance, the layers may be bonded, such as with an ultrasonic bond, to seal and preserve the pre-prepared substance therein. The assembled cartridge 60 can then be placed within the air passageway of the example electronic vaporizing device so that flow of heated air through the porous layer 63 vaporizes the selected substance disposed within, which then passes through the porous layer and into the mouthpiece for inhalation by a user, thereby allowing the selected substance to be loaded into the device and vaporized by the passage of heated air through the porous layer. In some embodiments, both the upper and lower layer are porous allowing flow of heated air through the cartridge. In other embodiments, the cartridge may include opposing outer layers where one is porous, while the other is non-porous so that heated air passes through the porous layer and is re-directed by the opposing non-porous layer before being inhaled. This aspect may improve vaporizing of the substance within the cartridge as the non-porous layer may retain more heat allowing for more uniform and efficient heating of the cartridge and the substance therein. In some embodiments, the non-porous layer may comprise metal or other heat conducting or heat retaining properties so as to assist in heating and vaporization of the material disposed within the cartridge. In some embodiments, the cartridge may be sealed and pierced by insertion to the grinding chamber or other cavity.

Figure 13A:
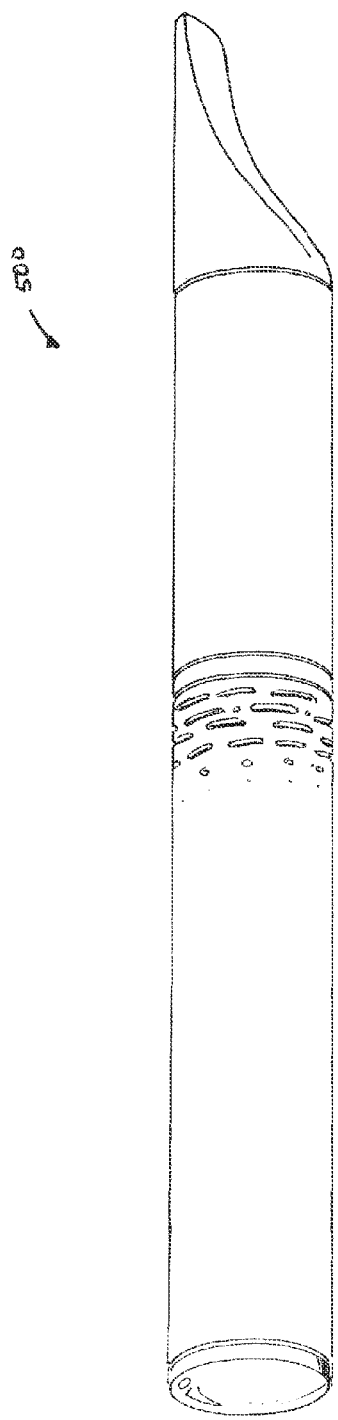
FIGS. 13A-13B illustrate another example vaporizing device.
Figure 13B:
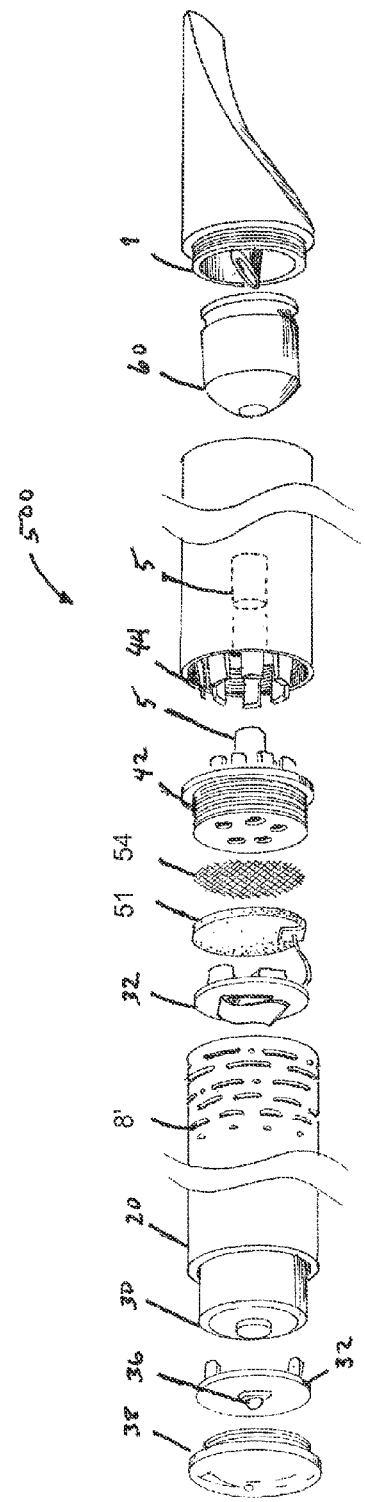

FIGS. 13A-13B illustrate an example embodiment of a device 500, which depicts alternative configurations of many of the components described above. As can be appreciated, the device may include a variety of differing mouthpiece 1 components. In certain embodiments, the mouthpiece portion 1 may be configured, such as through dimensioning and/or the incorporation of heat conducting or insulating materials, so as to ensure heated air withdrawn through the device is sufficiently cool for inhalation by a user. In the embodiment shown, the air is drawn through intake vents 8' in the side of the main body housing, although the device could be configured so that the distal air intake extends through the center of the distal lens tip, such as shown in FIGS. 6A-6D. Additionally, the distal air intake may also serve as the access to the charging port. In such embodiments, the distal lens may be fixedly attached to the main body, since the power source can be recharged without removing the distal lens tip. The air is drawn through a conduit extending through the distal lens tip and through the inhalation sensor disposed proximal of the lens tip. This configuration is advantageous in that combining the air intake through a main air intake that flows through the inhalation sensor allows for more rapid detection of a change in pressure due to inhalation, in this case a vacuum pressure, so as to further reduce the lag time from inhalation to vaporization of the selected substance.

Figure 17:
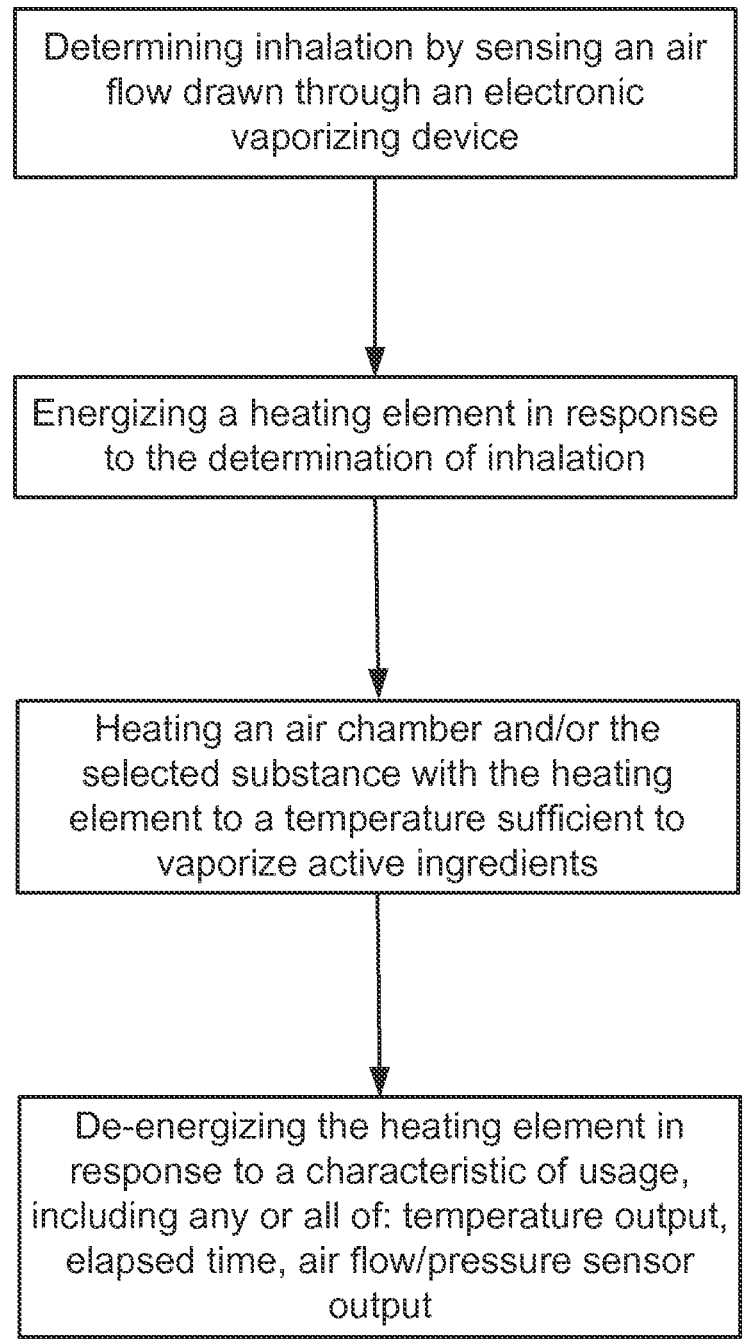
FIGS. 17-19 illustrate methods in accordance with certain embodiments of the invention.
Figure 18:
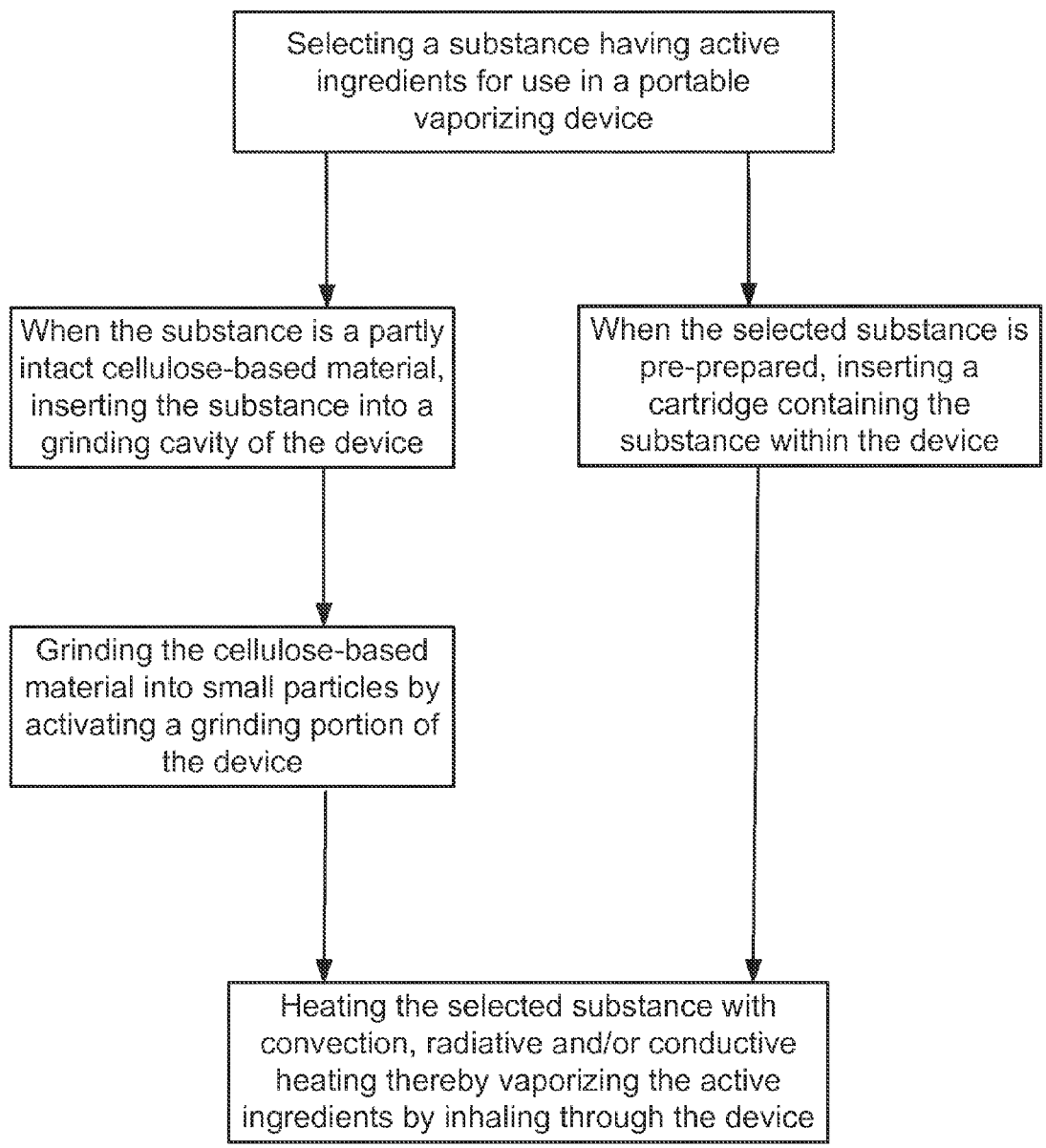
Figure 19:
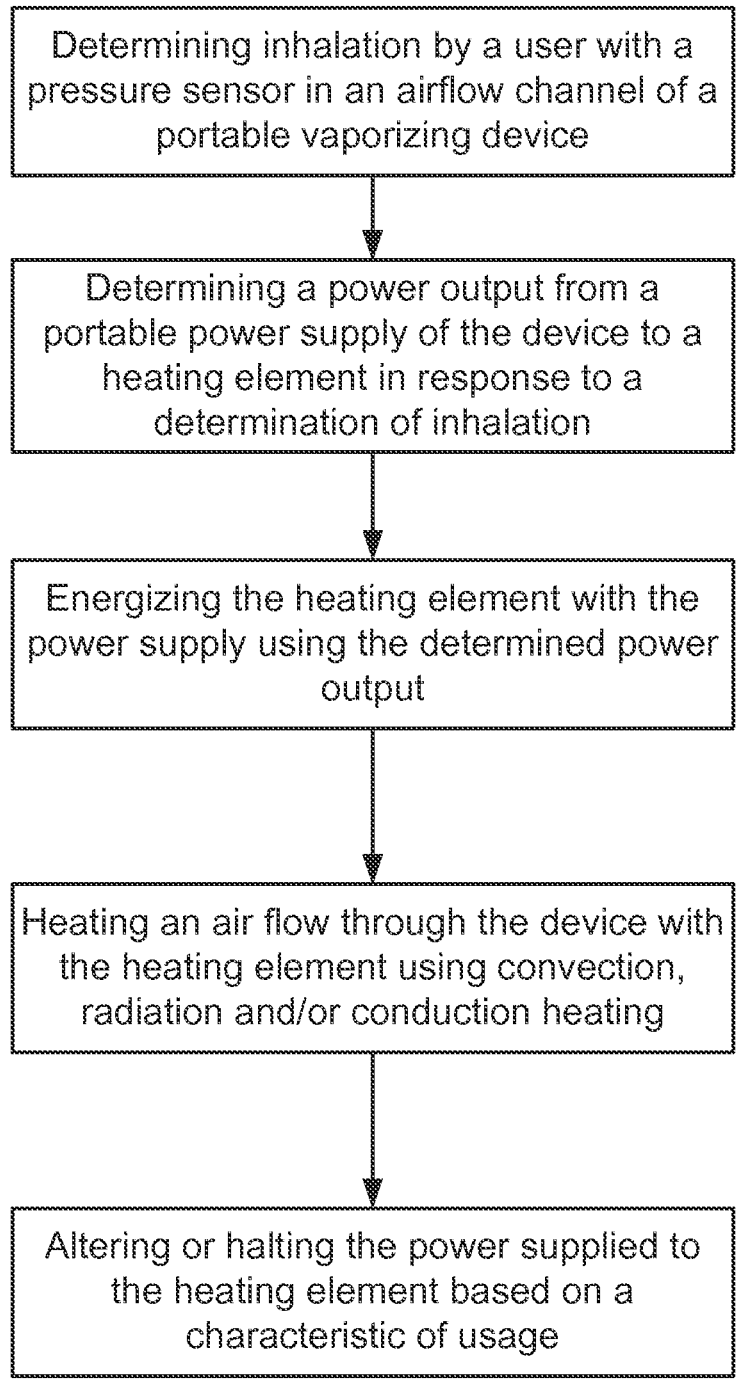

FIGS. 17-19 illustrate methods of vaporizing active ingredients of a selected substance with a vaporizing device, in accordance with many embodiments. In certain aspects, a control method for use in an example device is shown in FIG. 17, the method comprising: determining inhalation by sensing an air flow drawn through the device, energizing a heating element of the device in response to the determination of inhalation, heating an air chamber with the heating element to temperature sufficient to vaporize the selected substance, and de-energizing the heating element in response to a characteristic of usage, which may include any or all of a temperature output from a thermistor of the device, an elapsed time after inhalation, and an output from an air flow or pressure sensor of the device. In another aspect, a method of usage for an example device includes: selecting a substance to be vaporized within the portable vaporizing device; when the selected substance includes intact pieces of cellulose-based plant material, such as tobacco leaves or other plants or herbs, inserting the selected substance into a grinding cavity of the device and activating a grinding portion of the device; or when the selected substance is a pre-prepared substance, inserting a cartridge containing the pre-prepared substance within the device; and heating the pre-prepared substance with convection, conduction and/or radiative heating thereby vaporizing the active ingredients in the pre-prepared substance for inhalation by the user. In another aspect, control methods for powering an example device are provided, the method comprising: determining inhalation by a user with a pressure sensor in an airflow channel of a portable vaporizing device; determining a power output from a portable power supply of the device to a heating element in response to a determination of inhalation; energizing the heating element with the power supply using the determined power output; heating an air flow through the device with the heating element using convection and radiative heating; and altering or halting the power supplied to the heating element based on a characteristic of usage. It is appreciated that any of the steps of the methods may include any of the features or aspects described herein in accordance with many embodiments of the present invention.

While the above provides a complete description of particular embodiments, various alternatives, modifications, and equivalents may be used. One of skill in the art would appreciate that various features of separate embodiments may be combined in accordance with the principles of the invention, and that any of the above described features could be used or combined in a variety of ways in various types of vaporization devices. Therefore, the above description should not be taken as limiting the scope which is defined by the appended claims.

What is claimed is:

1. A portable electrically powered vaporizing device comprising:
    an outer housing having an axial passageway extending therethrough that allows inhalation of air from a distal portion through a proximal portion of the device, wherein the axial passageway includes a receptacle for holding a selected substance having an active ingredient selected by a user;
    a portable power source;
    a heating portion disposed within the axial passageway, the heating portion including a heating element for heating the selected substance within the receptacle to a desired temperature sufficient to vaporize the active ingredient of the selected substance for inhalation by a user; and
    a grinder portion for grinding the selected substance when the selected substance comprises cellulose-based material, the grinder portion defining an enclosed interior grinding cavity within the axial passageway of the outer housing, the interior grinding cavity being accessible by a user to allow the selected substance to be placed within the grinding cavity,
    wherein the grinder portion includes a proximal and distal grinding portion relative the axial passageway, wherein the proximal and distal grinding portions are securely coupleable so that, in combination, the proximal and distal grinding portions define the grinding cavity when coupled, and remain securely coupled during vaporizing with the device, wherein the proximal grinding portion is removable such that the grinding cavity is accessible to the user, and
    wherein one or both of the proximal and distal grinder portions include one or more teeth protruding from an interior portion of the respective grinder portion, a plurality of holes being disposed outside of the interior portion having the one or more teeth.

2. The portable vaporizing device of claim 1, wherein the heating element is positioned within the axial passageway and configured so as to heat the air and vaporize the active ingredient of the selected substance substantially without any combustion of the selected substance as air flows across the heating element.

3. The portable vaporizing device of claim 2, wherein the heating portion includes a reflector for reflecting radiation from the heating element so as to radiatively heat the air flowing through the passageway.

4. The portable vaporizing device of claim 1, wherein the power source is configured to energize the heating element in response to a determination of inhalation by a sensor so as to vaporize the active ingredient of the selected substance substantially without any combustion of the selected substance.

5. The portable vaporizing device of claim 1, wherein the power source is configured to determine and alter a power output to the heating element in response to an output from any or all of a thermistor, a capacitive type sensor, a piezo resistive element, and an elapsed time so as to provide a desired vaporization temperature while preserving heating element life and conserving power to extend battery life.

6. The portable vaporizing device of claim 1, wherein the heating element comprises a nichrome coil.

7. The portable vaporizing device of claim 1, wherein the desired temperature is within a range from about 170° C. to 200° C.

8. The portable vaporizing device of claim 1, wherein the power source is configured to heat the heating element so as to provide the desired vaporization temperature within three second or less after detection of inhalation.

9. The portable vaporizing device of claim 1, wherein the power source supplied to the heating portion is less than 30 Watts.

10. The portable vaporizing device of claim 1, wherein the power source is configured to energize the heating element according to a duty cycle.

11. The portable vaporizing device of claim 1 further comprising:
a recharging port electrically coupled with the power source so as to recharge the power source when coupled with an external power source.

12. The portable vaporizing device of claim 1 further comprising:
a distal light source electrically coupled with the power source, wherein the distal light source is configured to output light in response to a determination of inhalation with a sensor.

13. The portable vaporizing device of claim 1 wherein the distal light source is configured to provide an indicator of a state of the device, wherein the state of the device includes any or all of: a low level of power, a fully recharged state, a low level of the selected substance, damage to the device, and a recharging state.

14. The portable vaporizing device of claim 1, wherein the grinding cavity is disposed within the proximal portion of the device.

15. The portable vaporizing device of claim 1, wherein each of the proximal and distal grinding portions includes teeth extending into the grinding cavity when coupled, and wherein the proximal and distal grinding portions are separable from each other so as to allow a user to access and insert the selected substance within the grinding cavity.

16. The portable vaporizing device of claim 15, wherein the proximal and distal grinder portions are rotatable relative to each other so as to move the teeth of each portion in opposite directions when rotated so as to grind a solid substance when placed within the grinding cavity.

17. The portable vaporizing device of claim 1, wherein the proximal and distal portions are securely coupleable by a plurality of magnets, wherein the proximal grinder portion includes one or more magnets of the plurality interfaceable with one or more corresponding magnets of the plurality disposed in the distal grinder portion.

18. The portable vaporizing device of claim 1 further comprising:
a cartridge for containing a pre-prepared substance having active ingredients for vaporization, the cartridge configured for insertion into the grinding chamber by a user, wherein the cartridge optionally includes coloring and/or flavorings.

19. The portable vaporizing device of claim 1 wherein the heating element comprises a bulb heater.

20. The portable vaporizing device of claim 19 wherein the bulb heater comprises a tungsten filament in quartz halogen bulb.

21. The portable vaporizing device of claim 1 further comprising:
one or more screens for filtering particles associated with vaporization of the selected substance; and
a cleaning tool removably coupleable with the device, the cleaning tool adapted for cleaning or removing filtered particles from the one or more screens.

22. The portable vaporizing device of claim 1, wherein each of the proximal and distal grinding portions includes a plurality of holes so as to allow distributed flow of heated air through the grinding cavity so as to vaporize the active ingredient of the selected substance within the cavity.

23. The portable vaporizing device of claim 1, further comprising one or more magnets disposed within the proximal and/or the distal grinder portion so as to securely couple the proximal and distal grinder portions during vaporizing with the device while still allowing ready removal of the proximal grinder portion.

24. The portable vaporizing device of claim 1, wherein the proximal and distal grinder portions each include at least four magnets distributed about interfacing surfaces of the respective grinder portions at corresponding positions so that the at least four magnets engage each other when the proximal and distal grinder portions are fitted together thereby securely coupling the proximal and distal grinder portions during vaporizing with the device while still allowing ready removal of the proximal grinder portion.

25. The portable vaporizing device of claim 24, wherein the proximal and distal grinder portions have a cylindrical interface so as to facilitate rotation of the respective grinder portions relative to each other and the housing has a cross-sectional shape of a square with rounded corners, wherein the at least four magnets comprises a magnet positioned at each corner of the square cross-sectional shape.

26. A portable electrically powered vaporizing device comprising:
an outer housing having an axial passageway extending therethrough that allows inhalation of air from a distal portion through a proximal portion of the device, wherein the axial passageway includes a receptacle for holding a selected substance having an active ingredient selected by a user;
a portable power source;
a heating portion disposed within the axial passageway, the heating portion including a heating element for heating the selected substance within the receptacle to a desired temperature sufficient to vaporize the active ingredient of the selected substance for inhalation by a user; and
a grinder portion for grinding the selected substance when the selected substance comprises cellulose-based material, the grinder portion defining an enclosed interior grinding cavity within the axial passageway of the outer housing, the interior grinding cavity being accessible by a user to allow the selected substance to be placed within the grinding cavity,
wherein the grinder portion includes a proximal and distal grinding portion relative the axial passageway, wherein the proximal and distal grinding portions are securely coupleable so that, in combination, the proximal and distal grinding portions define the grinding cavity when coupled, and remain securely coupled during vaporizing with the device, wherein the proximal grinding portion is removable such that the grinding cavity is accessible to the user, wherein each of the proximal and distal grinding portions includes teeth extending into the grinding cavity when coupled, and wherein the proximal and distal grinding portions are separable from each other so as to allow a user to access and insert the selected substance within the grinding cavity, wherein the proximal and distal grinder portions are rotatable relative to each other so as to move the teeth of each portion in opposite directions when rotated so as to grind a solid substance when placed within the grinding cavity, and wherein the proximal and distal grinder portions each include an undulating surface, the undulating surface of the proximal portion interfaceable with the undulating surface of the distal grinder portion, wherein the undulating surface translates rotational movement into axial movement so that when the portions are rotated relative to each other during grinding, engagement of one undulating surface against the other undulating surface causes axial back and forth movement of the grinder portions relative to each other when the portions are coupled so as to facilitate break down of the selected substance within the grinding cavity.

27. A portable electrically powered vaporizing device comprising:

an outer housing having an axial passageway extending therethrough that allows inhalation of air from a distal portion through a proximal portion of the device, wherein the axial passageway includes a receptacle for holding a selected substance having an active ingredient selected by a user;

a portable power source;

a heating portion disposed within the axial passageway, the heating portion including a heating element for heating the selected substance within the receptacle to a desired temperature sufficient to vaporize the active ingredient of the selected substance for inhalation by a user; and a grinder portion for grinding the selected substance when the selected substance comprises cellulose-based material, the grinder portion defining an enclosed interior grinding cavity within the axial passageway of the outer housing, the interior grinding cavity being accessible by a user to allow the selected substance to be placed within the grinding cavity, wherein the grinder portion includes a proximal and distal grinding portion relative the axial passageway, wherein the proximal and distal grinding portions are securely coupleable so that, in combination, the proximal and distal grinding portions define the grinding cavity when coupled, and remain securely coupled during vaporizing with the device, wherein the proximal grinding portion is removable such that the grinding cavity is accessible to the user, and wherein the proximal and distal grinder portions each include an undulating surface, the undulating surface of the proximal portion interfaceable with the undulating surface of the distal grinder portion when rotating the proximal and distal grinder portions relative each other during grinding.

* * * * *